(12) United States Patent
Vogt et al.

(10) Patent No.: US 12,193,709 B2
(45) Date of Patent: Jan. 14, 2025

(54) DEVICE FOR LOCAL ADMINISTRATION OF PHARMACEUTICAL FLUIDS

(71) Applicant: Heraeus Medical GmbH, Wehrheim (DE)

(72) Inventors: Sebastian Vogt, Wehrheim (DE); Thomas Kluge, Wehrheim (DE)

(73) Assignee: Heraeus Medical GmbH, Wehrheim (DE)

( * ) Notice: Subject to any disclaimer, the term of this patent is extended or adjusted under 35 U.S.C. 154(b) by 568 days.

(21) Appl. No.: 17/110,608

(22) Filed: Dec. 3, 2020

(65) Prior Publication Data
US 2021/0169524 A1 Jun. 10, 2021

(30) Foreign Application Priority Data
Dec. 5, 2019 (EP) ..................... 19213716

(51) Int. Cl.
A61B 17/34 (2006.01)
(52) U.S. Cl.
CPC ...... *A61B 17/3472* (2013.01); *A61B 17/3415* (2013.01); *A61B 17/3421* (2013.01)
(58) Field of Classification Search
CPC .. A61M 5/14248; A61M 5/158; A61M 5/329; A61M 25/02; A61M 25/0618; A61M 25/0625; A61M 25/0631; A61M 25/0606; A61M 2005/14252; A61M 2005/1585; A61M 2005/1583; A61M 5/3298; A61M 2005/3201; A61M 2005/1587;
(Continued)

(56) References Cited

U.S. PATENT DOCUMENTS

| 4,362,156 A * | 12/1982 | Feller, Jr. .......... A61M 25/0637 604/177 |
| 4,861,341 A | 8/1989 | Woodburn |
| 5,601,559 A | 2/1997 | Melker et al. |

(Continued)

FOREIGN PATENT DOCUMENTS

| DE | 3334595 A1 | 4/1985 |
| DE | 3508759 A1 | 10/1985 |

(Continued)

OTHER PUBLICATIONS

Search Report mailed Feb. 20, 2020 by the European Patent Office for priority European Patent Application No. 19213716.4.
(Continued)

*Primary Examiner* — Tiffany Legette
(74) *Attorney, Agent, or Firm* — Dicke, Billig & Czaja, PLLC

(57) ABSTRACT

A device for local administration of pharmaceutical fluids. The device has at least one capillary with at least one opening in the region of its distal end, a hollow intermediate piece which is connected with the at least one capillary so as to allow the passage of liquid, a guide for directing the intermediate piece which comprises a distal support for resting on the patient, and a fixing element for fixing the intermediate piece to the guide. The fixing element allows fixing of the intermediate piece in various positions relative to the guide. Such fixation prevents displacement of the intermediate piece in relation to the guide. Also disclosed is a method for preparing such a device.

22 Claims, 15 Drawing Sheets

(58) Field of Classification Search
CPC ....... A61M 2005/1586; A61B 17/3421; A61B 17/3415; A61B 17/347; A61B 17/3401
See application file for complete search history.

(56) References Cited

U.S. PATENT DOCUMENTS

| | | | |
|---|---|---|---|
| 5,836,915 A * | 11/1998 | Steinbach | A61M 5/14276 604/131 |
| 5,871,470 A * | 2/1999 | McWha | A61B 17/3401 604/158 |
| 6,048,343 A | 4/2000 | Mathis et al. | |
| 6,214,012 B1 | 4/2001 | Karpman et al. | |
| 6,245,044 B1 * | 6/2001 | Daw | A61B 17/3401 604/164.11 |
| 6,866,648 B2 * | 3/2005 | Hadzic | A61M 5/486 604/512 |
| 8,382,808 B2 | 2/2013 | Wilberg et al. | |
| 8,974,505 B2 | 3/2015 | Sawa et al. | |
| 9,326,801 B2 | 5/2016 | Poulos | |
| 9,616,205 B2 | 4/2017 | Nebosky et al. | |
| 10,188,442 B2 | 1/2019 | Mazel | |
| 10,349,993 B2 | 7/2019 | Nebosky et al. | |
| 10,357,298 B2 | 7/2019 | Nebosky et al. | |
| 2001/0021852 A1 | 9/2001 | Chappius | |
| 2003/0069543 A1 | 4/2003 | Carpenter et al. | |
| 2003/0158520 A1 | 8/2003 | Safabash et al. | |
| 2004/0158207 A1 | 8/2004 | Hunn et al. | |
| 2005/0015059 A1 | 1/2005 | Sweeney | |
| 2005/0090801 A1 * | 4/2005 | Racz | A61M 25/0606 604/500 |
| 2007/0078432 A1 | 4/2007 | Halseth et al. | |
| 2007/0156103 A1 * | 7/2007 | Chatlynne | A61M 5/152 604/257 |
| 2009/0227987 A1 * | 9/2009 | Singer | A61B 17/3401 604/540 |
| 2011/0054416 A1 | 3/2011 | Hollowell et al. | |
| 2012/0029578 A1 | 2/2012 | Suh | |
| 2012/0316513 A1 | 12/2012 | Sharkey et al. | |
| 2013/0237958 A1 * | 9/2013 | Arrigo | A61B 17/3401 604/164.01 |
| 2014/0209197 A1 * | 7/2014 | Carrez | F16L 29/005 137/798 |
| 2017/0265746 A1 | 9/2017 | Rajendran et al. | |
| 2017/0290977 A1 | 10/2017 | Schauderna | |
| 2019/0275237 A1 | 9/2019 | Barmaimon et al. | |

FOREIGN PATENT DOCUMENTS

| | | |
|---|---|---|
| DE | 3429038 A1 | 2/1986 |
| DE | 2843963 C2 | 2/1988 |
| DE | 3203957 C2 | 12/1989 |
| EP | 0305417 B1 | 6/1995 |
| EP | 0595782 B1 | 6/1998 |
| EP | 1350478 | 10/2003 |
| EP | 1622529 B1 | 12/2011 |
| EP | 2887899 B1 | 8/2017 |
| JP | 2017526482 A | 9/2017 |
| RU | 2572481 C1 | 1/2016 |
| RU | 2622613 C2 | 6/2017 |
| WO | 2007/051161 A1 | 5/2007 |
| WO | 2014/049887 A1 | 4/2014 |

OTHER PUBLICATIONS

Examination Report mailed Aug. 17, 2021 by IP Australia for counterpart Australian Patent Application No. 2020256328.

Office Action for counterpart Japanese Patent Application No. 2020-202207 dispatched Sep. 27, 2021 by the Japanese Patent Office (with English translation attached).

* cited by examiner

DEVICE FOR LOCAL ADMINISTRATION OF PHARMACEUTICAL FLUIDS

RELATED APPLICATION

This application claims the benefit of priority to European Patent Application Number EP 19213716.4, filed on Dec. 5, 2019, the contents of which are incorporated in this application by reference.

TECHNICAL FIELD

The invention relates to a device for local administration of pharmaceutical fluids and to a method for preparing such a device prior to medical use.

BACKGROUND OF THE DISCLOSURE

The local administration of active pharmaceutical ingredients such as antibiotics has been known for decades and has proven particularly useful in the treatment or easing of bone tissue infections. In this respect, a distinction may be drawn between non-absorbable and absorbable or biodegradable active ingredient vehicles.

A plurality of successful treatment options, such as for example the use of osteosynthesis plates, intramedullary nails and external fixators have been established for decades for treating bone fractures. A distinction is drawn between closed and open bone fractures. In closed fractures, the fracture is completely covered by soft tissue. These fractures are generally easy to treat. Cases of complications in the form of peri-implant infections seldom arise, in around just one percent of cases. In contrast, in open fractures the fractured bones are not enclosed or are only partially enclosed by soft tissue as a result of soft tissue injury. Until medical care is provided, open fractures are unprotected and exposed to exogenous contamination with microbial microorganisms. Microbial microorganisms may thereby come into direct contact with the open bone tissue. In surgical treatment of open fractures, it is conventional to clean the exposed bone tissue intensively. To this end, for example, lavage systems are used to remove bone tissue contamination as far as possible by rinsing. Systemic antibiotic prophylaxis is also conventional. Unfortunately, however, in roughly 25 percent of cases the bone tissue becomes infected by microbial microorganisms.

If early or late infection occurs in fractures, all foreign materials present, such as osteosynthesis plates, screws, pins etc., are removed and debridement is carried out. Then systemic antibiotic treatment, combined with local antibiotic vehicles, such as for example collagen sponges containing gentamicin and polymethyl methacrylate chains, is conventionally used to ease the infections, wherein the fractured bones are simultaneously stabilized by osteosynthesis materials. Examples of absorbable or biodegradable active ingredient vehicles are nonwovens and sponges of collagen or gelatin. Documents DE 34 29 038 A1, DE 33 34 595 A1, DE 28 43 963 C2, DE 32 03 957 C2 and DE 33 34 595 A1 are stated by way of example. These vehicles contain gentamicin sulfate or mixtures of gentamicin sulfate and a sparingly water-soluble gentamicin salt. Furthermore, there are a plurality of absorbable or biodegradable active ingredient vehicles based on tricalcium phosphate, hydroxyapatite, gypsum and mixtures thereof and also composite materials of these salts and organic binders.

One disadvantage of the listed non-absorbable and indeed absorbable or biodegradable active ingredient vehicles is that the antimicrobial active ingredient is fixed by the selected composition and that after implantation of the active ingredient vehicle the active ingredient can no longer be replaced with or supplemented by other active ingredients. Furthermore, in all previous local active ingredient release systems, active ingredient release is based on the principle of diffusion, such that large quantities of active ingredient are only released in the first few hours. One exception is the use of sparingly water-soluble active ingredient salts, for which active ingredient release depends on the solubility equilibrium of the active ingredient salts.

Periprosthetic infections represent a very serious complication for the patient. These infections can become chronic and develop into chronic osteitis, which is very difficult to treat. In addition, the treatment of periprosthetic infections is also associated with high financial cost and material usage.

It is therefore desirable, in the case of open fractures, to prevent colonization of the fractured bone tissue by microbial microorganisms as early as possible by local administration of antibiotics at the potentially contaminated fracture surfaces of the bone tissue.

In this respect, an active ingredient vehicle is desirable which allows local administration of any desired active pharmaceutical ingredient and wherein the active pharmaceutical ingredient may be supplemented at any time by other fluid active pharmaceutical ingredients. Moreover, it is desirable for the active ingredient concentration which is obtained directly at the fracture to be adjustable directly from outside.

Bone screws with a central channel in the screw body and windows connected thereto are known as cannulated and fenestrated screws. These bone screws, in the form of cannulated-fenestrated pedicle screws, have previously been used substantially in the spine region. In this case, bone cement paste is injected through the screw channel into the generally osteoporotic vertebra. A cement mantle generally forms which is coaxial with the longitudinal axis of the pedicle screw. The bone cement then hardens and forms an abutment for the pedicle screws. A plurality of cannulated and fenestrated bone screws have been proposed. Patent specifications and published patent applications DE 35 08 759 A1, RU 2 572 481 C1, RU 2 622 613 C2, US 2001/0021852 A1, US 2005/0015059 A1, US 2012/0029578 A1, U.S. Pat. No. 6,214,012 B1, U.S. Pat. No. 9,326,801 B2, U.S. Pat. No. 8,382,808 B2 and U.S. Pat. No. 8,974,505 B2 are examples of cannulated and fenestrated bone screws.

A special cannulated and fenestrated bone screw is described in EP 1 622 529 B1. A guide element is disclosed as inserted temporarily into the bone screw channel. The guide element facilitates the injection of bone cement paste.

A similar adapter for implanting a cannulated and fenestrated bone screw is disclosed in U.S. Pat. No. 6,048,343 A. The adapter has a longitudinal channel and seals the proximal bone screw bore with its outer wall, such that liquids can be injected into the bone screw through the adapter. The adapter is removed once the liquid has been injected into the bone.

A screw described in U.S. Pat. No. 10,188,442 B2 is intended for tumor treatment and has three or more longitudinal channels in the screw body, these being fenestrated. These longitudinal channels are provided for connection to catheters. With catheters connected to the screw, liquid active ingredients can be administered into the bone surrounding the screw.

A bone screw provided with longitudinal through-slits, in which the screw head also has longitudinal slits, is proposed in EP 2 887 899 B1. The longitudinal slits in the screw body are intended to enable a better release of substances, such as bone cement, from the bone screw.

Patent EP 0 305 417 B1 describes a bone screw which is cannulated and fenestrated. This bone screw is screwed into the bone in a vacuum-tight manner. A suction rinsing system is described with this bone screw. In this case, a rinsing liquid is introduced with one cannulated and fenestrated bone screw and the rinsing liquid is sucked off by vacuum at a second cannulated and fenestrated bone screw.

U.S. Pat. No. 5,601,559 A1 describes a cannulated and fenestrated bone screw which is intended to allow systemic administration of active pharmaceutical ingredients via the bone tissue as an alternative to venous access.

A self-tapping bone screw with longitudinal slits and a central channel is disclosed in EP 0 595 782 B1. The slits and the channel are initially intended to take up bone material cut during tapping of the screw and then to allow the bone tissue to grow together with the bone screw. A slit having a plurality of openings to the internal channel extends into the thread but not as far as the screw head. The channel and the slits are blocked by bone material on tapping of the bone screw and can then no longer be used to convey a pharmaceutical fluid.

U.S. Pat. Nos. 10,357,298 B2, 10,349,993 B2 and 9,616,205 B2 disclose implants and an implantable screw, which contains a longitudinal channel with fenestrations. A distally enlarging taper is arranged in the longitudinal channel, below a screw head. Below this taper is a reservoir with outward-leading channels. The diameter of the longitudinal channel in the screw head is equal to the diameter of the reservoir. The length of the channels leading out from the reservoir is greater than the internal diameter of these channels.

The fenestrated bone screws known in the field have the disadvantage that they are not absolutely necessary for treating a simple fracture. Screwing in of the bone screws damages the adjacent bone, while in those cases in which the fractured bone can grow together even without using screws, no benefit is gained from the possibility of fastening with bone screws. Furthermore, the bone screws must remain in the patient or be removed in a complex operation, wherein this operation may again result in undesired infections.

SUMMARY OF THE DISCLOSURE

An object of the invention is to overcome the disadvantages of the prior art. In particular, a device is provided for local administration of pharmaceutical fluids, such as for example antibiotic solutions, which enables local and temporary delivery of the pharmaceutical fluid directly into the region of the bone, such as for example into infected fractured but already aligned bones. The device is also suitable for repeated delivery of the pharmaceutical fluid over relatively long periods at a specific site without the device having to be removed for this purpose. The device is relatively inexpensive to manufacture. The treatment procedure with the device is adaptable, so that it is possible to respond to a change in the treatment situation or to a lack of success. The device is easy to remove from the patient without a complex operation.

Another object of the invention consists in developing a device in the form of a local administration system for pharmaceutical fluids which is intended for preventing and also treating periprosthetic infections in aligned fractured bones. The administration system enables local administration and preferably also rinsing with pharmaceutical fluids in the case of at least partial soft tissue coverage over a period of several hours to days. The intention is for any desired antiseptic or antibiotic solutions to be administrable in the region of a patient's bone requiring treatment.

Still another object of the invention consists in particular in developing a device for temporary local administration of pharmaceutical active ingredient solutions into bone tissue, specifically into the fracture gap of fractured bones. The device can be inserted into the fracture gap directly on reduction of the fractured bones and growing together of the bone tissue can proceed largely unhindered. The device allows active ingredient administration within bones over a period of several hours to days. This is intended to counteract colonization of the bone tissue with microbial microorganisms. It is possible to administer aqueous active ingredient solutions of any desired composition using the device. The device has a surface such that ingrowth of connective tissue into the device is not possible. Once active ingredient administration has been completed, the device can be removed as simply and carefully as possible. What is important is for the device to be such that the active ingredient solutions can be administered at the specified position in the bone and the device cannot be displaced from this position by unintentional external application of tension during administration of the active ingredient solution.

One or more of the objects underlying the invention are achieved by a device for local administration of pharmaceutical fluids, the device comprising:

at least one capillary with at least one opening in the region of the distal end of the at least one capillary, a hollow intermediate piece, which is connected with the at least one capillary so as to allow passage of liquid, a guide for guiding the intermediate piece, which comprises a distal support for resting on the patient, and a fixing element for fixing the intermediate piece to the guide, wherein the fixing element allows fixing of the intermediate piece in various positions relative to the guide, wherein the fixing prevents displacement of the intermediate piece in relation to the guide.

The term "capillary" is understood according to the invention as a hollow tube with an external diameter of at most 3 mm, preferably of at most 2 mm and particularly preferably of at most 1 mm. The terms "distal" or "distal end" are used to define the part or surface of an element which is facing the patient or positioned furthest from the user. The terms "proximal" or "proximal end" are used to define the part of surface of an element which is facing away from the patient or positioned closest to the user.

The distal support is produced according to the invention by a distal support surface for resting on a patient surface. Preferably, the support is a perforated disk, which forms a distal end of the guide. In this way, the guide rests well against the surface of the patient's body. This disk may be fastened simply with plaster to the surface of the skin or may be sewn onto the skin.

A core can be arranged in a cavity of the at least one capillary and of the intermediate piece, wherein the core is removable from the cavity of the at least one capillary, wherein the core closes at least 50% of the cross-sectional area of the at least one opening, and wherein the core is releasably connected with the intermediate piece in such a way that the connection limits or prevents axial movement of the core in the cavity of the at least one capillary.

The core can be cylindrical in shape.

The core can be releasably anchored to the intermediate piece.

Preferably, the core is manually removable from the cavity of the at least one capillary and the intermediate piece. It may theoretically be sufficient for the core to be removable from the at least one capillary and for the part of the core previously closing the at least one capillary to remain in the cavity of the intermediate piece. The cavity of the intermediate piece has a larger internal diameter than the at least one capillary, such that the pharmaceutical fluid can flow straightforwardly through the cavity of the intermediate piece past the part of the core previously closing the at least one capillary, which part of the core is then arranged in the cavity of the intermediate piece.

The core can be a thin wire or thread for closing the at least one opening of an individual capillary or the core can be a bundle of thin wires with individual ends or a bundle of thin threads with individual ends for closing the at least one opening of a plurality of capillaries. In this way, the core may be drawn more readily out of the capillaries and the intermediate piece.

The core can have at least one distal end with a thickened portion for closing the at least one opening of the at least one capillary.

The core can close at least 50% of the cross-sectional area of the cavity of the at least one capillary as far as the at least one opening, in particular as far as the opening of the at least one opening arranged closest to the distal end of the at least one capillary.

Moreover, the fixing element allows mechanical fixing of the intermediate piece to the guide. Alternatively, magnetic fixing would also be conceivable, for example.

Preferably, fixing of the intermediate piece to the guide prevents axial movement of the core in relation to the cavity of the at least one capillary during deformation of the at least one capillary and preferably also during deformation of the intermediate piece.

Fixing of the intermediate piece to the guide also prevents to axial movement of the core in relation to the cavity of the at least one capillary during implantation.

For the purposes of the present invention, the core is capable of being drawn out of the cavity of the at least one capillary by an adapter and preferably also of being drawn out of the cavity of the hollow intermediate piece.

In this way, the core can be drawn out of the at least one capillary after implantation, in order to allow passage of a pharmaceutical fluid. The adapter is preferably arranged, in particular fastened, at the proximal end of the intermediate piece. The adapter may then preferably also be used for connection of a source for the pharmaceutical fluid, particularly preferably for producing a fluid-tight connection. The source for the pharmaceutical fluid can in particular be a syringe.

Moreover, the device includes a tube which is connected or connectable with the intermediate piece for passage of liquid, wherein the tube is deformable.

In this way, the device can be separated from the source of the pharmaceutical fluid by the tube, such that when the source moves, the device is not exposed to mechanical load. A syringe may preferably be used as the source. The tube also allows the source to be separate from the device.

The tube is preferably deformable.

The intermediate piece can be connected or connectable for passage of liquid with a fluid reservoir, in particular via the above-mentioned tube, wherein a pharmaceutical fluid can be forced out of the fluid reservoir under pressure through the intermediate piece and through the at least one capillary and, where present, also through the tube, and out of the at least one opening of the at least one capillary.

This configuration enables direct passage of the pharmaceutical fluid through the device.

Moreover, the intermediate piece can be hollow-cylindrical or tubular, wherein the intermediate piece preferably has a taper at its distal end connected to the at least one capillary, preferably a conical taper, wherein particularly preferably the conical taper is a hollow cone.

In this way, the structure is particularly inexpensive to produce and the pharmaceutical fluid can flow readily through the intermediate piece into the at least one capillary.

Furthermore, the intermediate piece can be arranged axially movably in the guide when the fixing provided by the fixing element is released.

In this way, the intermediate piece may be guided by and in the guide when the fixing is released and the at least one capillary thereby positioned with the device.

The guide can be hollow-cylindrical or tubular.

The intermediate piece may thereby be guided with the at least one capillary in the guide without major resistance.

According to a preferred further development of the present invention, the core can be releasably connected with the intermediate piece by a thread or a bayonet closure.

In this way, a stable but also simply releasable connection may be provided between the core and the intermediate piece. The user can undo this connection without difficulty.

The fixing element can be a retaining device or a clamping device arranged on the guide, in particular clamping jaws capable of being screwed together, or the fixing element can be a screw, in particular a wing screw, wherein preferably the screw is screwed or screwable into a bore with an inner thread extending through a wall of the guide, such that the intermediate piece is capable of being clamped in the guide with a front end of the screw.

In this way, the intermediate piece may be simply fixed in any position relative to the guide. A clamping device and a screw may also be used together as a double fixing element.

As an alternative to the screw, a clamping device may be arranged on the guide for mechanical fixing of the intermediate piece. For the purposes of the invention, catch devices or releasable hook-and-loop connections or releasable adhesive connections can be used to fix the intermediate piece.

The intermediate piece can be clamped to the guide by the fixing element in any desired axial position. The intermediate piece may thereby be fixed in any desired position on the guide. In this way, the precise extent may in turn be established by which the at least one capillary projects out of the guide and thus to what depth in the patient, in particular in the patient's bone, the distal end or ends of the at least one capillary is or are arranged.

Moreover, the intermediate piece allows passage of liquids when the intermediate piece is fixed in the guide by the fixing element.

In this way, it may be ensured that the pharmaceutical fluid can be forced through the fixed intermediate piece into the at least one capillary. This means that the fixing by the fixing element does not close the cavity of the intermediate piece.

The cavity of the guide can be at least as long as the length of the at least one capillary or as the length of the longest capillary of the at least one capillary.

In this way, it is ensured that the at least one capillary can be let fully into the guide and thus can be stored safely in the guide.

Preferably, the cavity in the guide tapers at the distal end, in particular continuously tapers or conically tapers, and a hole is arranged at the distal end of the tapering region, in particular at a tip of a cone, through which hole the at least one capillary is guided or guidable through the distal end of the guide, wherein the diameter of the hole is preferably smaller than the external diameter of the intermediate piece.

In this way, the at least one capillary can be advanced out of the guide while being held by the guide. The in particular conical taper allows the at least one capillary to be inserted into the guide without difficulty on assembly of the device.

It is also proposed with the present invention that the device comprise a container for the pharmaceutical fluid, wherein a pharmaceutical fluid particularly preferably containing at least one antibiotic active ingredient, at least one antimycotic active ingredient and/or at least one chemotherapeutic agent, is contained in the container.

In this way, the device is further completed and can be used directly for treatment.

Moreover, the container can comprise a hollow cylinder with a plunger displaceable axially in the hollow cylinder, the plunger closing a first end of the hollow cylinder, wherein the hollow cylinder has a discharge opening at an opposite end from the first end, the discharge opening being connected or connectable with a proximal end of the intermediate piece, preferably being connected or connectable with the proximal end of the intermediate piece via a manually operable valve element for regulating the flow velocity of the pharmaceutical fluid.

The container may be connected to the proximal end of the intermediate piece via the tube. The tube may thus be arranged between the container and the intermediate piece. The proximal end of the intermediate piece is opposite the distal end of the intermediate piece at which the at least one capillary is arranged.

The device comprises a delivery mechanism with which the pharmaceutical fluid can be forced out of a container connected or connectable with the delivery mechanism into the intermediate piece and through the at least one capillary and through the at least one opening into the surrounding environment of the at least one capillary, wherein preferably the delivery mechanism has an energy storage element, in particular at least one tensioned spring, wherein the delivery mechanism is drivable with energy from the energy storage element, wherein a plunger in a hollow cylinder may be driven as the container towards an opposing discharge opening particularly preferably with the energy storage element.

With a delivery mechanism, the device may be used directly to generate a volumetric flow of the pharmaceutical fluid. If the delivery mechanism comprises an energy storage element, the device does not have to be connected to an external power supply to drive the delivery mechanism. A tensioned spring contains sufficient energy to enable the device to expel a quantity of a few milliliters to a few centiliters of the pharmaceutical fluid.

Moreover, the core projects beyond an at least one distal opening arranged closest to the distal end of the at least one capillary to the extent that, on bending of the at least one capillary, this at least one distal opening is closed over at least 50% of the cross-sectional area of this opening.

In this way, it is ensured that the at least one distal opening of the at least one capillary remains closed even on bending of the at least one capillary. This prevents tissue residues or other impurities from being able to penetrate into the at least one opening or into the at least one capillary and clogging it. In this way, tissue constituents are prevented from clogging the at least one capillary during implantation even on bending of the at least one capillary. It is advantageous for the core to project roughly 3 mm relative to the at least one opening of the at least one capillary.

According to a further development of the present invention, the at least one capillary is at least two capillaries, wherein the at least two capillaries are of different lengths, preferably all the capillaries of the at least two capillaries are of different lengths.

In this way, treatment may proceed at different depths with the same release of the pharmaceutical fluid. It is advantageous for the at least two liquid-permeable capillaries connected with the intermediate piece to be of different lengths. It is thereby possible to supply different regions of the fracture gap locally with active ingredient solutions.

Preferably, the at least one capillary consists of titanium, of special steel or of plastic material, in particular of a dimensionally stable plastic material.

These materials are biocompatible and well suited to producing the at least one capillary. In addition, all other biocompatible metal alloys may be used. Another possibility is to use high strength glass capillaries or ceramic capillaries which, however, are then not or barely deformable.

Moreover, a porous sponge-like disk can be arranged at the distal end of the guide, wherein the porous sponge-like disk preferably contains an antiseptic liquid, in particular an antiseptic solution.

In this way, the surroundings of the inlet channel into the patient's body are kept free of microorganisms or the microbial count is kept low during medical use of the device. In this way, the entry of microorganisms into the channel in which the at least one capillary is arranged may be prevented or reduced. This prevents additional infection. The porous sponge-like disk loaded with antiseptic prevents microbial microorganisms from migrating along the at least one capillary into the soft and bone tissue.

The at least one capillary and the core can be deformable, wherein the at least one capillary is preferably plastically deformable.

In this way, the shape of the at least one capillary may be adapted to the treatment situation. In addition, the guide may also be or have been bent.

The fact that the at least one capillary is deformable means that the at least one capillary can be non-destructively deformed to a limited extent. To a limited extent means that the at least one capillary may be bent but not folded. The same applies to the core.

Preferably, the at least one capillary is non-destructively deformable by bending (but not by folding). A fold may particularly preferably be present if a radius of curvature falls below 0.1 mm, particularly preferably if a radius of curvature falls below 0.5 mm.

The at least one capillary is preferably plastically and/or elastically deformable.

The at least one capillary is preferably axially deformable and particularly preferably not radially deformable or only if handled incorrectly. The term axially relates to the direction of conduction of the at least one capillary.

The objects addressed by the present invention are also achieved by a method for preparing a device for local administration of pharmaceutical fluids according to the invention prior to medical use, having the following steps taking place in a chronological sequence:

A) pushing the at least one capillary out of the guide by inserting the intermediate piece into the guide; and B) fixing the intermediate piece in the guide with the fixing element.

The method is preferably not used to treat a human or animal body. Medical treatment is obtained only by the addition and delivery of the pharmaceutical fluid, which are not part of the method according to the invention.

According to a preferred further development of the present invention, a core is arranged in the at least one capillary to remain arranged in the at least one capillary in step A), and preferably also in step B).

Thus, no medical treatment of a human or animal body which is excluded from patentability takes place in the method according to the invention.

It may be provided that in a step C) after step B) or after step A) the at least one capillary is shaped by plastic deformation of the at least one capillary.

A source of a pharmaceutical fluid or a container containing a pharmaceutical fluid can be connected to a proximal end of the intermediate piece, such that a fluid-conducting and/or fluid-tight connection arises between the source or the container and the cavity of the at least one capillary.

A porous sponge-like disk is or has been arranged at the distal end of the guide, wherein the porous sponge-like disk is impregnated or loaded with an antiseptic liquid, in particular an antiseptic solution.

The core may be removed from the cavity of the at least one capillary prior to insertion of the device. This step preferably takes place as the final step prior to medical use of the device or after insertion in the patient, in order to prevent clogging of the at least one opening of the at least one capillary.

In addition, the distal support may be fastened to the patient for treatment purposes, in particular adhesively bonded to the patient's skin.

Underlying the present invention are the surprising findings that it is possible, due to the at least one guided capillary, which is preferably closed with a removable core, and which can be locked in relation to a guide arrangeable on the patient, to provide a device which reliably enables local administration of pharmaceutical fluids at the join sites of fractured bones. The capillaries are preferably secured against clogging by the removable core. Once treatment is complete, the at least one capillary can be withdrawn carefully out of the bone in the process of growing together without bringing about heavy mechanical loading on the healing fracture. At the same time, pharmaceutical fluids for treating the fracture may be delivered into the fracture even during the healing process, so boosting the healing result. In addition, the treatment can be adjusted by the addition of different pharmaceutical fluids.

The device is used in such a way that first of all the desired position of the at least one opening of the at least one capillary in the fracture gap is determined at which the active ingredient solution is to be administered. Then the intermediate piece is pushed into the guide until the at least one capillary projects to such an extent out of the guide that, on placing the guide onto the body surface of the patient, the at least one capillary arrives precisely at the intended position in the fracture gap. Then the intermediate piece is fixed mechanically to the guide. In this way, the length of the at least one capillary is fixed. If two or more capillaries are used, then these are bent such that the cross-section of the fracture surface is sufficiently overlapped or covered. The thin capillaries only slightly impede the growth together of the bone tissue in the fracture gap. A minimal groove may also be introduced into the cortical bone, so that the one capillary or the plurality of capillaries may be placed into the fracture gap without the fracture ends being spaced apart from one another. The core is then released and withdrawn from the intermediate piece preferably only after successful reduction, such that the cavity of the capillary or the cavities of the capillaries is or are free. The intermediate piece can thereafter be connected with a tube or directly with a source of the pharmaceutical fluid. Aqueous active ingredient solutions can be simply injected into the device using conventional syringes. The active ingredient solution then flows through the tube via the intermediate piece into the at least one capillary and then exits from the distal opening or the distal openings. This makes it possible to locally achieve very high active ingredient concentrations directly at the fracture gap, which are used to treat the fracture. After a predetermined period of hours to days, the one capillary or the capillaries is or are simply withdrawn from the fracture gap. By "predetermined" is meant determined beforehand, so that the predetermined characteristic must be determined, i.e., chosen or at least known, in advance of some event.

An exemplary device according to the invention may be composed of:
 a) at least one plastically deformable capillary with at least one opening in the region of the distal end of the capillary,
 b) a hollow intermediate piece, which is connected with the at least one capillary so as to allow passage of liquid,
 c) an elastic tube, which is connected or connectable with the intermediate piece so as to allow passage of liquid,
 d) a guide for the intermediate piece, which has a distal support face for resting on the patient surface, and
 e) a fixing element for mechanically fixing the intermediate piece to the guide, whereby relative movement of the intermediate piece in relation to the guide is prevented,
 f) wherein a manually removable, plastically or elastically deformable cylindrical core is arranged in the cavity of the at least one capillary and of the intermediate piece prior to implantation, which core closes at least 50% of the cross-sectional area of the at least one opening of the at least one capillary, wherein after implantation the core is drawn by an adapter out of the cavity of the at least one capillary, and wherein
 g) the core is anchored releasably on the intermediate piece in such a way as to prevent axial movement of the core during implantation.

A further exemplary device according to the invention may be composed of:
 a) at least one plastically deformable capillary with at least one opening in the region of the distal end of the at least one capillary,
 b) a hollow-cylindrical intermediate piece, which is connected with the at least one capillary so as to allow passage of liquid,
 c) an elastic tube, which is connected or connectable with the intermediate piece so as to allow passage of liquid,
 d) a hollow-cylindrical guide, which has a distal support face for resting on the patient surface, wherein the hollow-cylindrical intermediate piece is arranged axially movably in the hollow-cylindrical guide, and
 e) a fixing element for mechanically fixing the intermediate piece to the guide, whereby relative movement of the hollow-cylindrical intermediate piece in relation to the guide is prevented,
 f) wherein a manually removable, plastically or elastically deformable cylindrical core is arranged in the cavity of the at least one capillary and of the intermediate piece prior to implantation, which core closes at least 50% of the cross-sectional area of the at least one opening of the at least one capillary, wherein after implantation the core is drawn by an adapter out of the cavity of the at least one capillary, and wherein g) the core is anchored releasably on the hollow-cylindrical intermediate piece by a thread or a bayonet closure in such a way as to prevent axial movement of the core during implantation.

BRIEF DESCRIPTION OF THE FIGURES

Further exemplary embodiments of the invention are explained below with reference to fifteen schematically depicted figures, but without thereby restricting the invention. In the figures.

DETAILED DESCRIPTION OF THE DISCLOSURE

Figure 1:
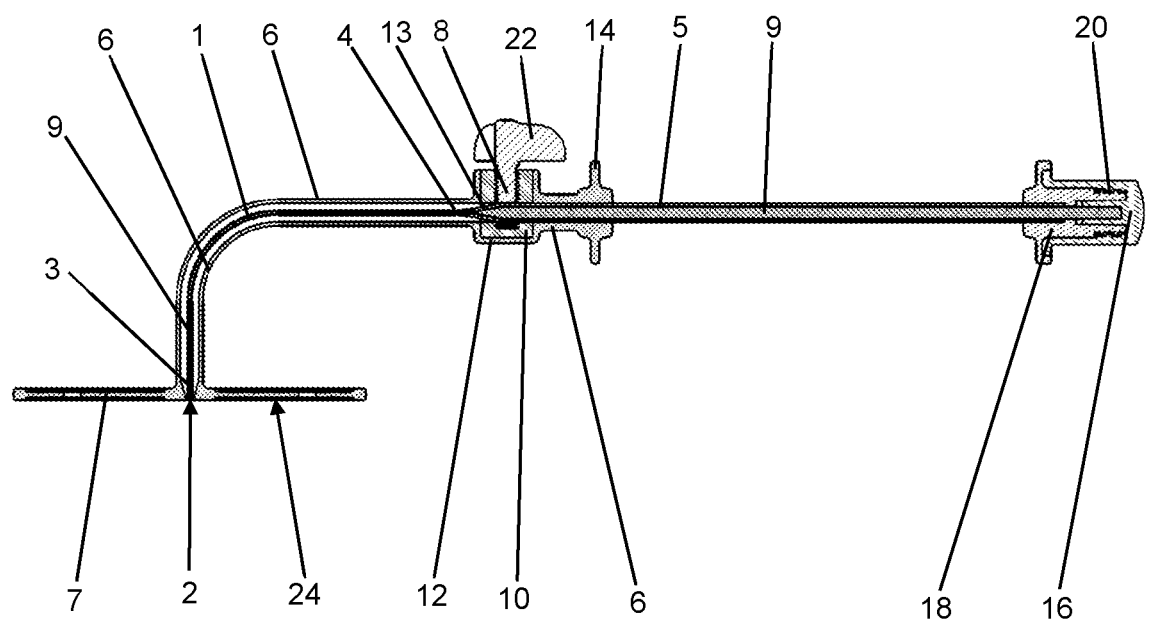
FIG. 1 shows a schematic cross-sectional view through a first device according to the invention for local administration of pharmaceutical fluids.

The present invention in particular provides a medical device for temporary, local administration of pharmaceutical fluids or of medical fluids over a period of a few hours up to several days. The device according to the invention is intended above all for the prevention and also treatment of periprosthetic fracture infections. The device according to the invention is provided as and suitable for an administration system for local administration of pharmaceutical fluids in and at the bone tissue, in particular in the medullary cavity, over a period of several hours to days.

In the figures and the following description of the exemplary embodiments of the present invention explained with reference to the figures, some of the same reference signs are used for the same or similar parts in different exemplary embodiments and for different individual parts so as to simplify comparability of the exemplary embodiments and readability.

FIGS. 1 to 10 and 12 to 14 show a first device according to the invention in different representations and in different situations. The device comprises a capillary 1. The capillary 1 has an opening 2 in a distal end 3 of the capillary 1. A plurality of openings (not shown) may also be provided, however, in the wall of the capillary 1.

At a proximal end 4 of the capillary 1 opposite the distal end 3, the capillary 1 is connected with a hollow intermediate piece 5. The capillary 1 delimits a cavity within it. The cavity of the capillary 1 may be connected with the cavity in the intermediate piece 5. In this way, the cavity of the capillary 1 may be connected in a fluid-conducting manner with the cavity of the intermediate piece 5, such that a medical fluid can be forced through the intermediate piece 5 into the capillary 1 and expelled through the opening 2 of the capillary 1.

The intermediate piece 5 may be firmly connected with the capillary 1. The intermediate piece 5 and the capillary 1 are arranged and directed in a plastically deformable guide 6. To this end, the intermediate piece 5 and the capillary 1 can be arranged movably within the guide 6. At its distal end the guide 6 has a support 7 in the form of a disk. The support 7 may be fastened to a patient, in order to fix the device to the patient. The support 7 may have a plurality of holes, allowing gas exchange between the patient's skin 60 and the surroundings. The distal bottom and also the proximal top of the support 7 may have recesses. Into these recesses a sponge (not shown) in the form of a circular disk (optionally with holes) may be inserted, which may be impregnated with a disinfecting solution. In this way, the surface of the skin 60 and thus the entrance site of the capillary 1 into the patient's body may be kept free of microorganisms. The sponge may be part of the device.

A fixing element 8 for fixing the intermediate piece 5 on the guide 6 is arranged in the guide 6. When the intermediate piece 5 is fixed on the guide 6 by the fixing element 8, the intermediate piece 5 can no longer be moved in relation to and in the guide 6 and the capillary 1 can consequently no longer be displaced axially in relation to the guide 6.

A withdrawable core 9, which closes the opening 2 of the capillary 1, is arranged in the interior of the capillary 1 and of the intermediate piece 5. The core 9 has a smaller internal diameter than the capillary 1. The opening 2 is preferably at least 50% closed. The core 9 may to this end project through the opening 2, in order to compensate movement of the core 9 in relation to the opening 2 on bending of the capillary 1. It may to this end be sufficient for the core 9 to protrude by at most 3 mm out of the opening 2 of the straight capillary 1, preferably for the core 9 to protrude by at most 1 mm out of the opening 2 of the straight capillary 1. The core 9 may be withdrawn from the proximal end of the intermediate piece 5 in order to open the opening 2 of the capillary 1.

The fixing element 8 may have an outer thread and be screwed into a matching seat 10 with inner thread in the manner of a screw in order to fix the intermediate piece 5 in the seat 10 and thus to the guide 6. To this end, the intermediate piece 5 may be guided through the seat 10. The guide 6 may have a receptacle 12 in which the seat 10 is inserted or fastened.

A hollow cone 13 is arranged at the point of transition from the intermediate piece 5 to the capillary 1. The hollow cone 13 may merge the internal diameters of the cavities of the capillary 1 and of the intermediate piece 5 into one another. To this end, the interior of the hollow cone 13 may taper conically towards the cavity of the capillary 1.

A limit stop 14 in the form of a protruding disk, which simplifies handling of the device, is arranged at a proximal end of the guide 6.

The core 9 is connected at its proximal end with a fastening cap 16, which may be screwed onto an adapter 18 with a matching outer thread 20. To this end, an inner thread 42 matching the outer thread 20 of the adapter 18 is arranged in the fastening cap 16. The adapter 18 may be fastened to the proximal end of the intermediate piece 5. The fastening cap 16 and the adapter 18 connect the core 9 with the intermediate piece 5 and thus with the capillary 1. By unscrewing the fastening cap 16 from the adapter 18, the core 9 may be released from the intermediate piece 5 and the capillary 1. Once the fastening cap 16 has been released, the core 9 can be withdrawn from the intermediate piece 5 and the capillary 1. In this way, the cavities inside the capillary 1 and the intermediate piece 5 can be opened and the opening 2 is opened. This prevents the opening 2 from being obstructed or clogged by soiling before removal of the core 9.

The fixing element 8 may be operated, or unscrewed and released, by using a twist handle 22. Once the fixing element 8 has been released using the twist handle 22, the intermediate piece 5 may be moved in relation to the guide 6.

The distal bottom of the support 6 forms a support face 24 for resting on the skin 60 or surface of a patient.

A syringe 26 (bottom right in FIG. 2) may be part of the device but also a separate part with which a pharmaceutical fluid may be injected into the device. The syringe 26 comprises a container 28 with a cylindrical interior for the pharmaceutical fluid. A plunger 30 is arranged axially movably in the cylindrical interior of the container 28. The plunger 30 may be pushed into the container 28 by using a plunger flange 32 in order to expel a medical or pharmaceutical fluid from the container 28. A connecting piece 34 with an inner thread is arranged at the front end of the syringe 26, so as to be able to connect the syringe 26 with the adapter 18. A closure 36 for closing the interior of the container 28 at the front end thereof is arranged at the tip of the connecting piece 34.

To connect the connecting piece 34 with the adapter 18 of the intermediate piece 5, a connecting adapter 38 with an outer thread 40 is provided. The outer thread 40 of the connecting adapter 38 may be used to produce a fluid-tight connection with the inner thread of the connecting piece 34 of the syringe 26. In this way, a fluid-tight connection between the interior of the container 28 of the syringe 26 and the cavity of the intermediate piece 5 may be produced by using the connecting adapter 38.

To extend the connection between the syringe 26 and the intermediate piece 5, a tube 44 is used. The tube 44 also has the advantage that it is deformable, such that on connection of the syringe 26 with the intermediate piece 5 via the tube 44, no forces are transferred from the syringe 26 to the intermediate piece 5 provided the tube 44 is loose and not taut. The tube 44 comprises a counter-adapter 46 for connection with the adapter 18 on the intermediate piece 5. Furthermore, the tube 44 has a connector 48 for connection with the connecting adapter 38. In this way, the tube 44 may provide a fluid-tight connection between the syringe 26 and the intermediate piece 5 (see FIGS. 6, 8, 9, and 10).

A filter 52 is arranged inside the connecting adapter 38, to prevent the passage of particles and/or microorganisms into the intermediate piece 5. This filter 52 is preferably a sterile filter. For the same purpose, a sterile filter (not shown) may be arranged in the adapter 18 or in the distal end of the cavity of the intermediate piece 5.

Figure 2:
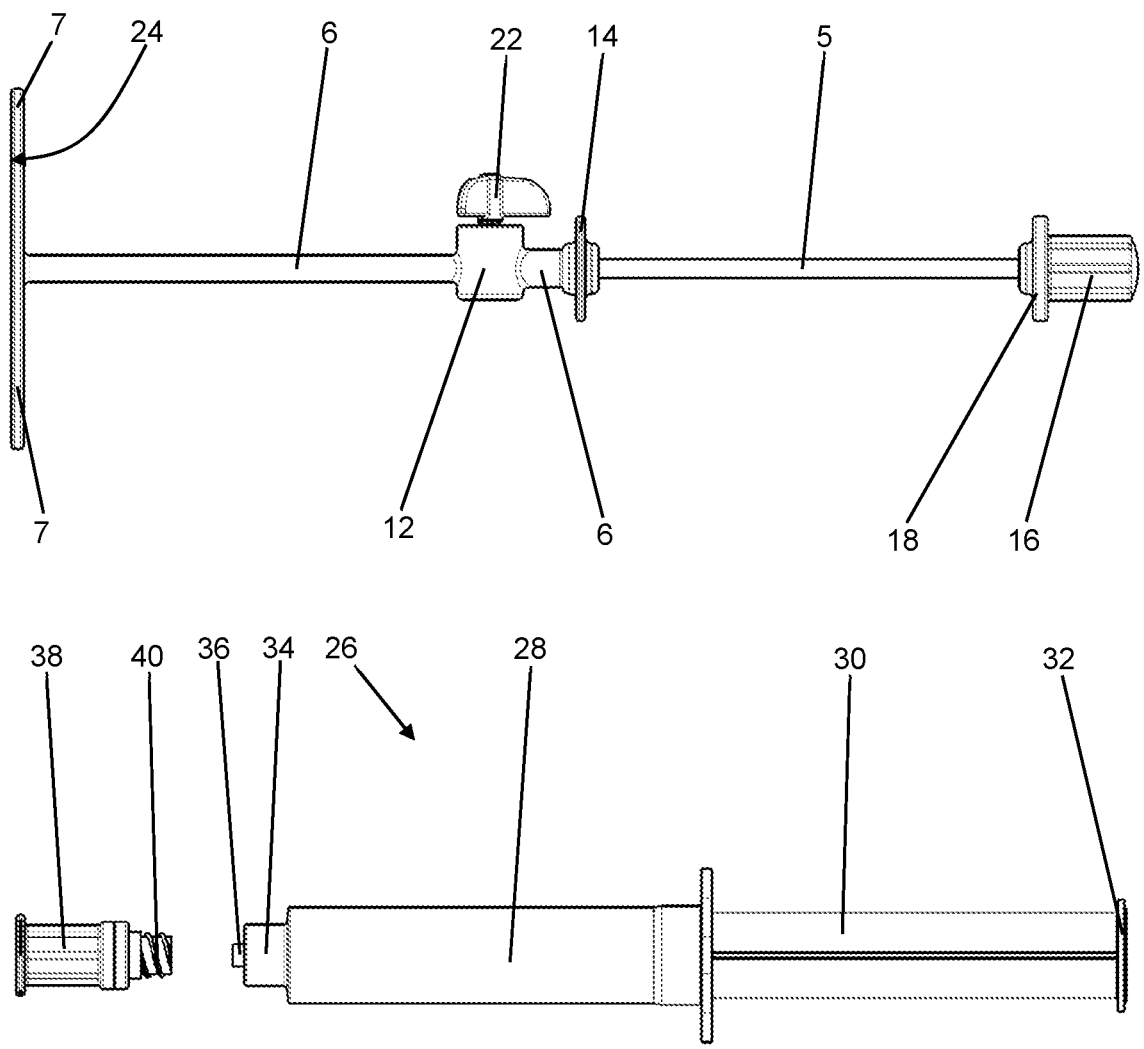
FIG. 2 shows a schematic side view of the device according to FIG. 1 with a straight guide and with a syringe and an adapter for injecting the fluid into the device.

The initial state of the first example device according to the invention is shown in FIGS. 1 and 2. The core 9 closes the cavity of the capillary 1 and the cavity of the intermediate piece 5. The core 9 is connected to the intermediate piece 5 via the fastening cap 16 with the adapter 18. The capillary 1 is fully retracted into the guide 6. The intermediate piece 5 projects proximally out of the guide 6. As shown in FIG. 1, the guide 6 may be bent or curved for use of the device. In this case, the capillary 1 and the core 9 in the capillary 1 are also bent or curved. The capillary 1 and the core 9 and the intermediate piece 5 are intended to be non-destructively bendable or curvable.

Figure 3:
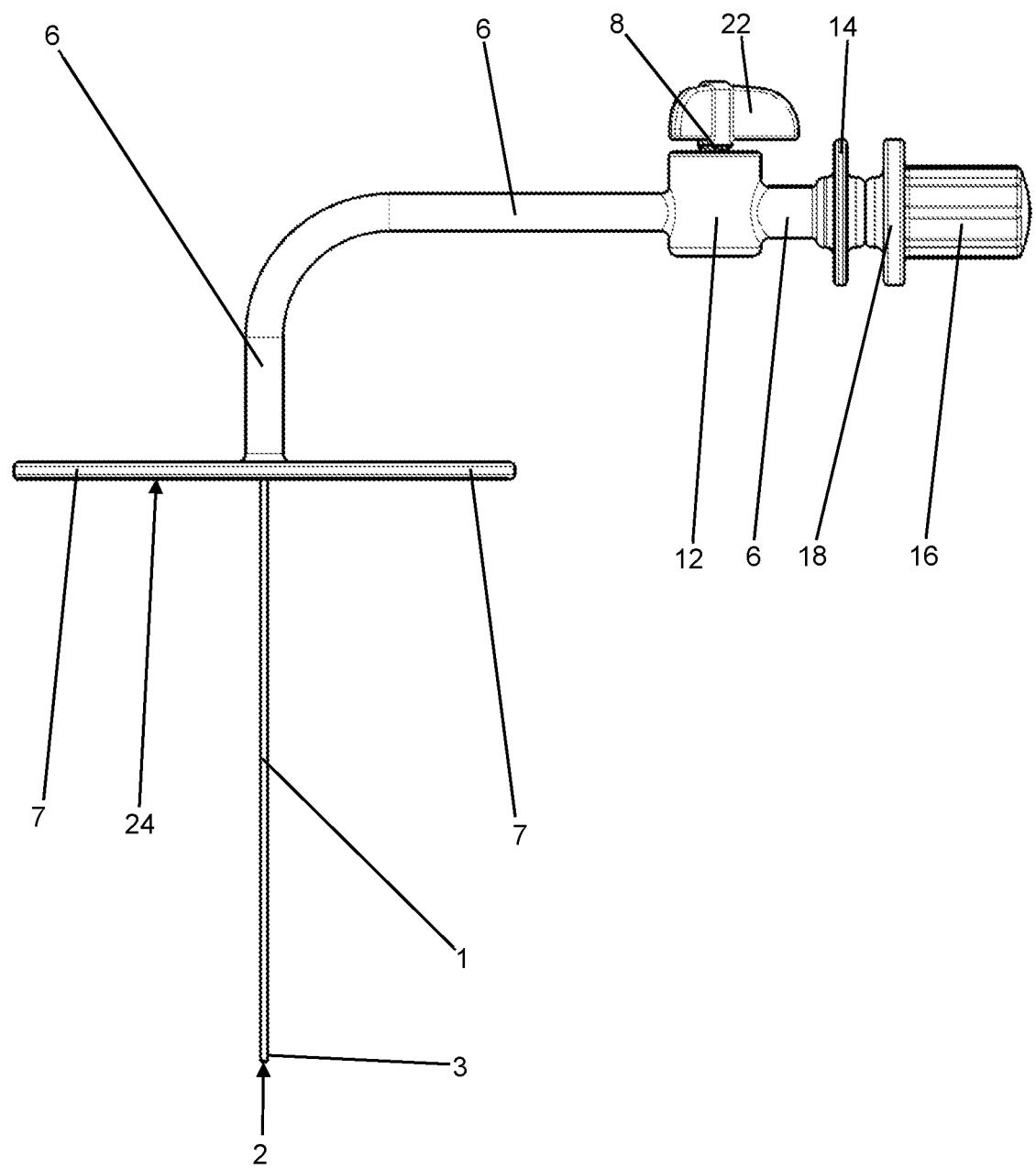
FIG. 3 shows a schematic side view of the device according to FIG. 1 with an extended capillary.

In the next step, the fixing element 8 is released. Then, the intermediate piece 5 is inserted into the guide 6. The capillary 1 then exits from the distal front end of the guide 6. On insertion of the intermediate piece 5, the intermediate piece 5 is curved by the guide 6. When the length of the capillary 1 projecting out of the guide 6 is as long as the user wants, the intermediate piece 5 is again fastened to the guide 6 by the fixing element 8. The intermediate piece 5 can thereafter no longer be moved in relation to the guide 6 and the length of the capillary 1 protruding from the guide 6 is fixed. In FIG. 3 the intermediate piece 5 has been inserted to the maximum degree into the guide 6. Then the adapter 18 impacts against the limit stop 14 and blocks further insertion, before the hollow cone 13 becomes wedged in the distal end of the guide 6. This situation is shown in FIG. 3.

Figure 4:
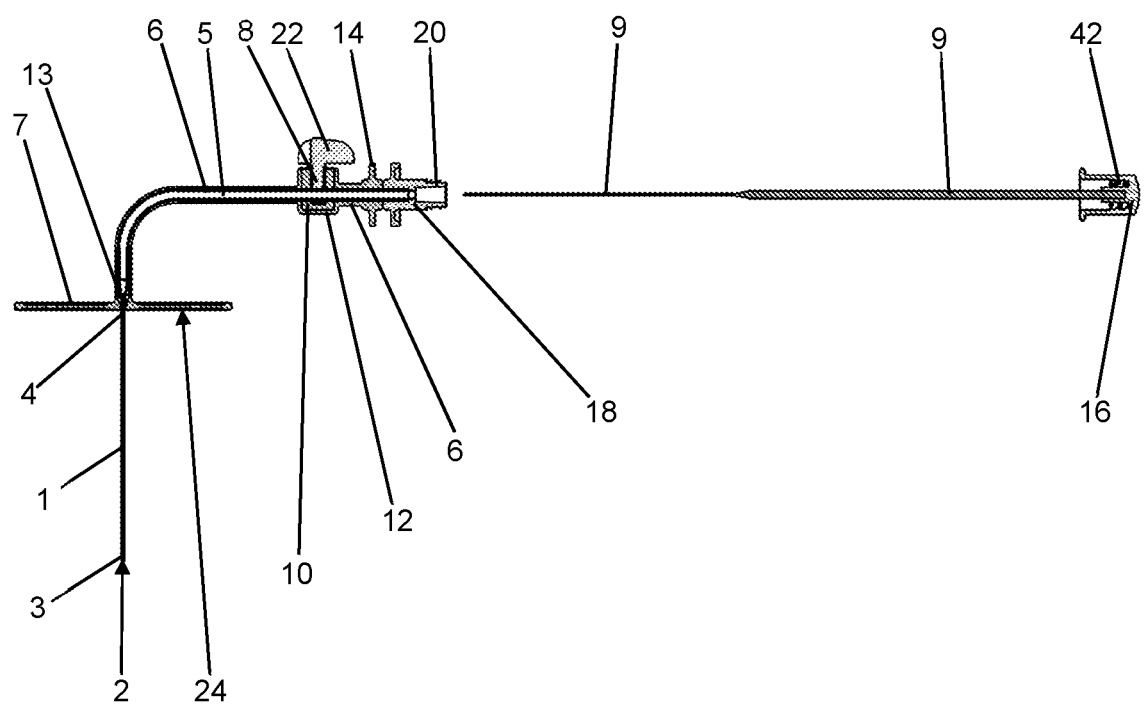
FIG. 4 shows a schematic cross-sectional view of the first device according to the invention according to FIGS. 1 to 3 with a withdrawn core.
Figure 5:
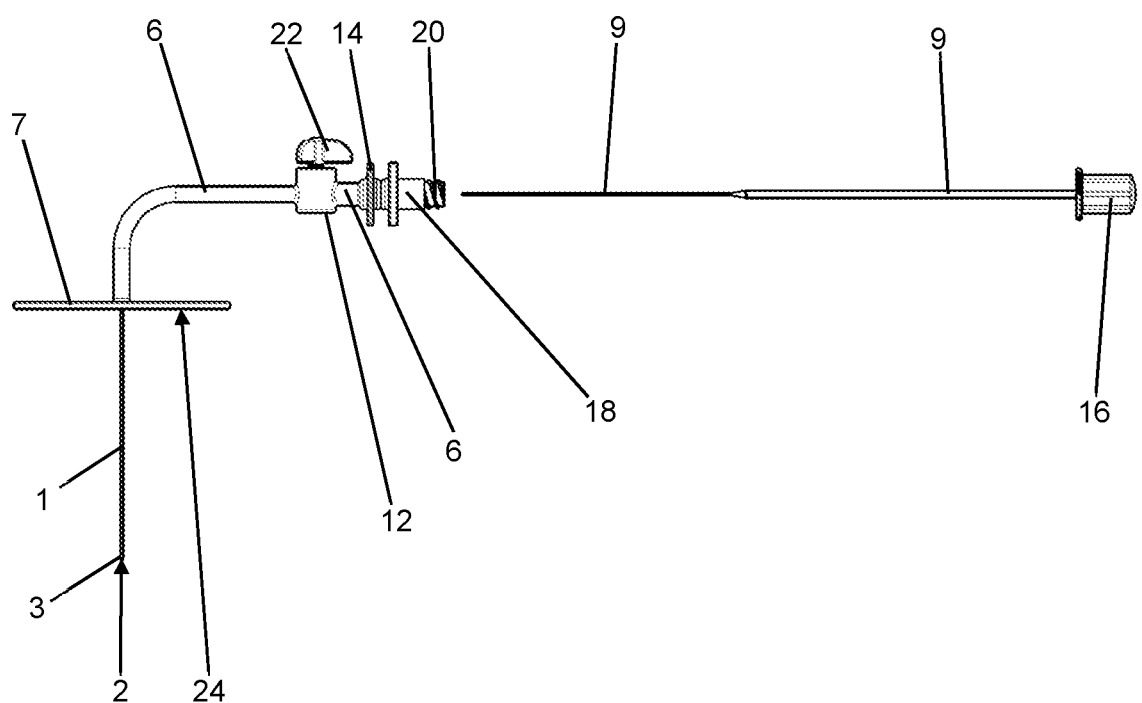
FIG. 5 shows a schematic side view of the first device according to the invention according to FIGS. 1 to 3 with a withdrawn core.

In the next step, the fastening cap 16 is screwed off the adapter 18 and the core 9 withdrawn from the capillary 1 and the intermediate piece 5. This situation is shown in FIGS. 4 and 5. The opening 2 at the distal end 3 of the capillary 1 is then opened.

Figure 6:
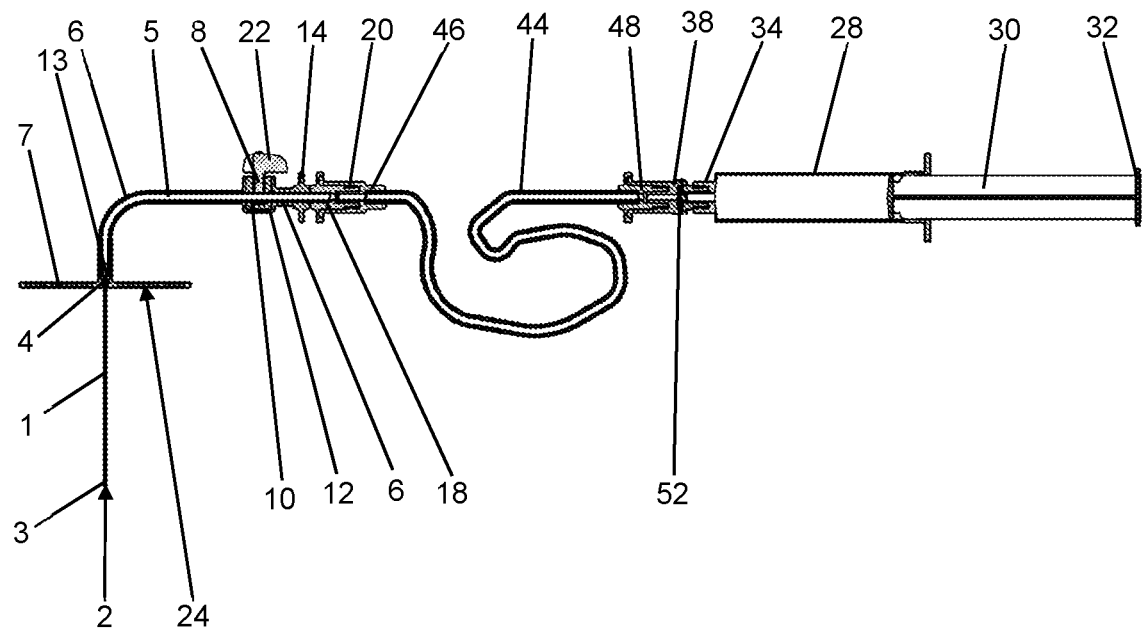
FIG. 6 shows a schematic cross-sectional view of the first device according to the invention with a syringe connected via a tube.
Figure 7:
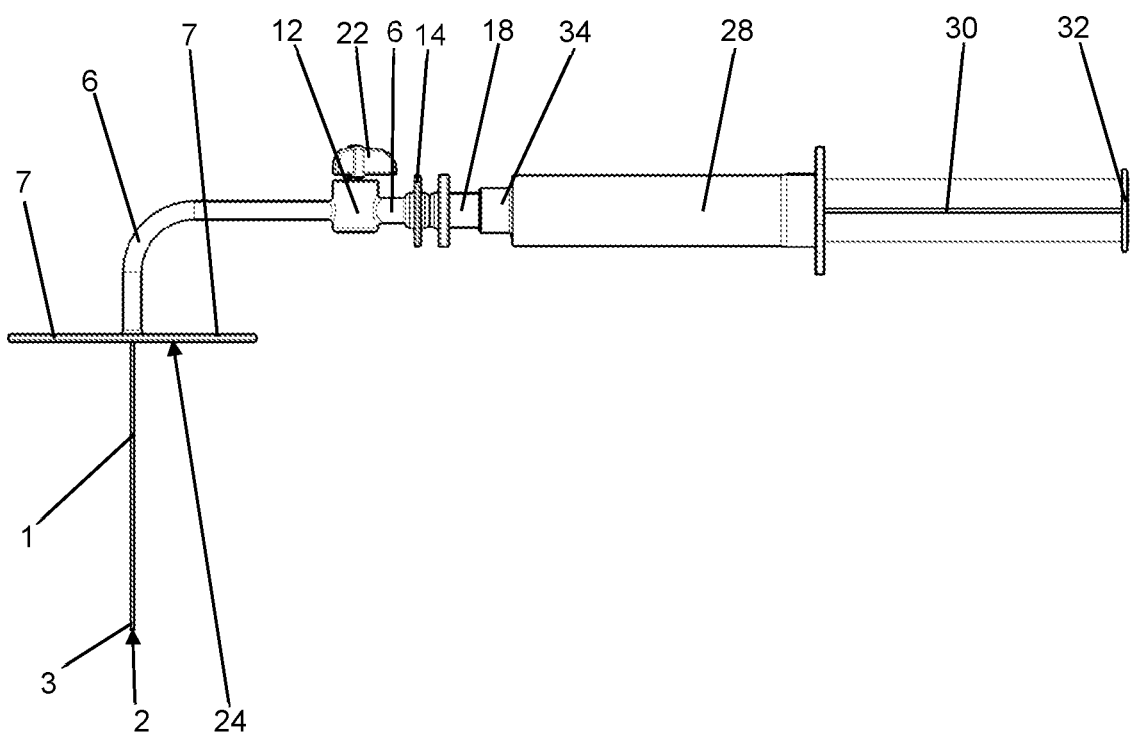
FIG. 7 shows a schematic side view of the first device according to the invention with a connected syringe.

The syringe 26, which may be filled with a pharmaceutical fluid, can then be connected directly (see FIG. 7) or via the tube 44 (see FIGS. 6 and 8 to 10) with the intermediate piece 5. This situation is shown in FIGS. 6 and 7.

Figure 8:
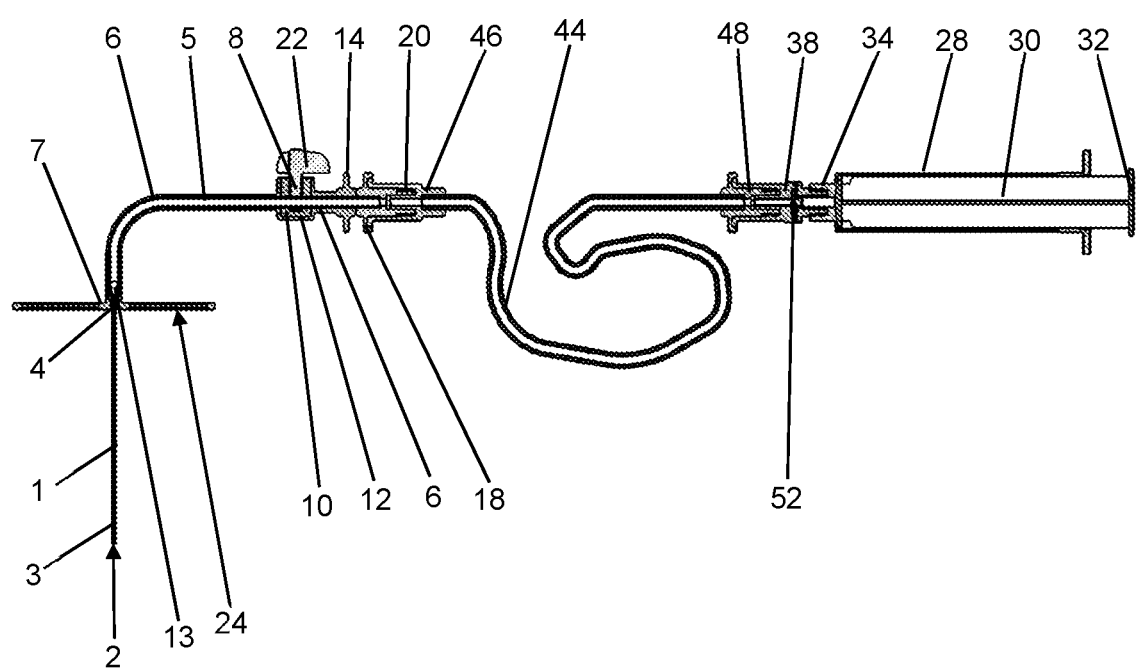
FIG. 8 shows a schematic cross-sectional view of the first device according to the invention with a syringe connected via a tube and squeezed.
Figure 9:
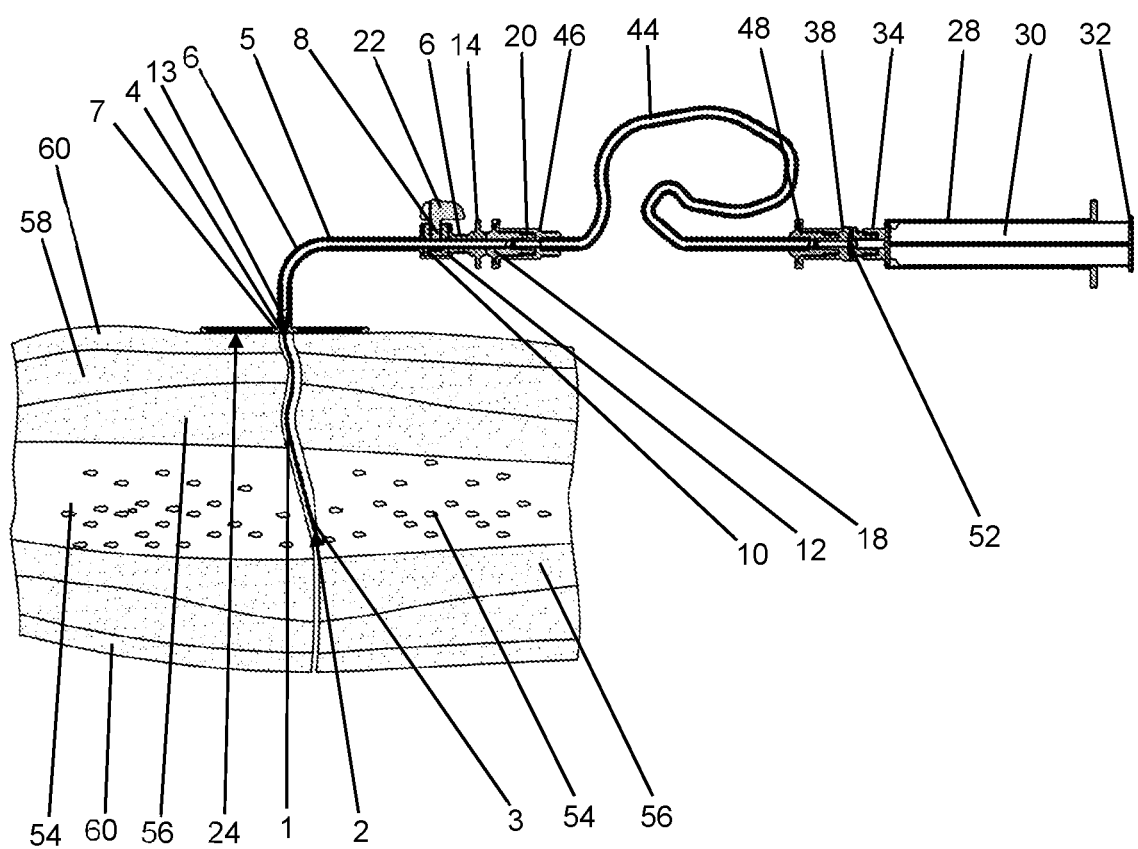
FIG. 9 shows a schematic cross-sectional view of the first device according to the invention during treatment with a syringe connected via a tube and squeezed.

The inside of the container 28 of the syringe 26 can then be injected via the adapter 18 and optionally the tube 44 into the intermediate piece 5 and the capillary 1. To this end, the plunger 30 is pressed into the container 28. This situation is shown in FIGS. 8 and 9. As an alternative to the syringe 26, a drip (not shown) may also be connected to the adapter 18, in order to feed a medical fluid into the device.

Figure 10:
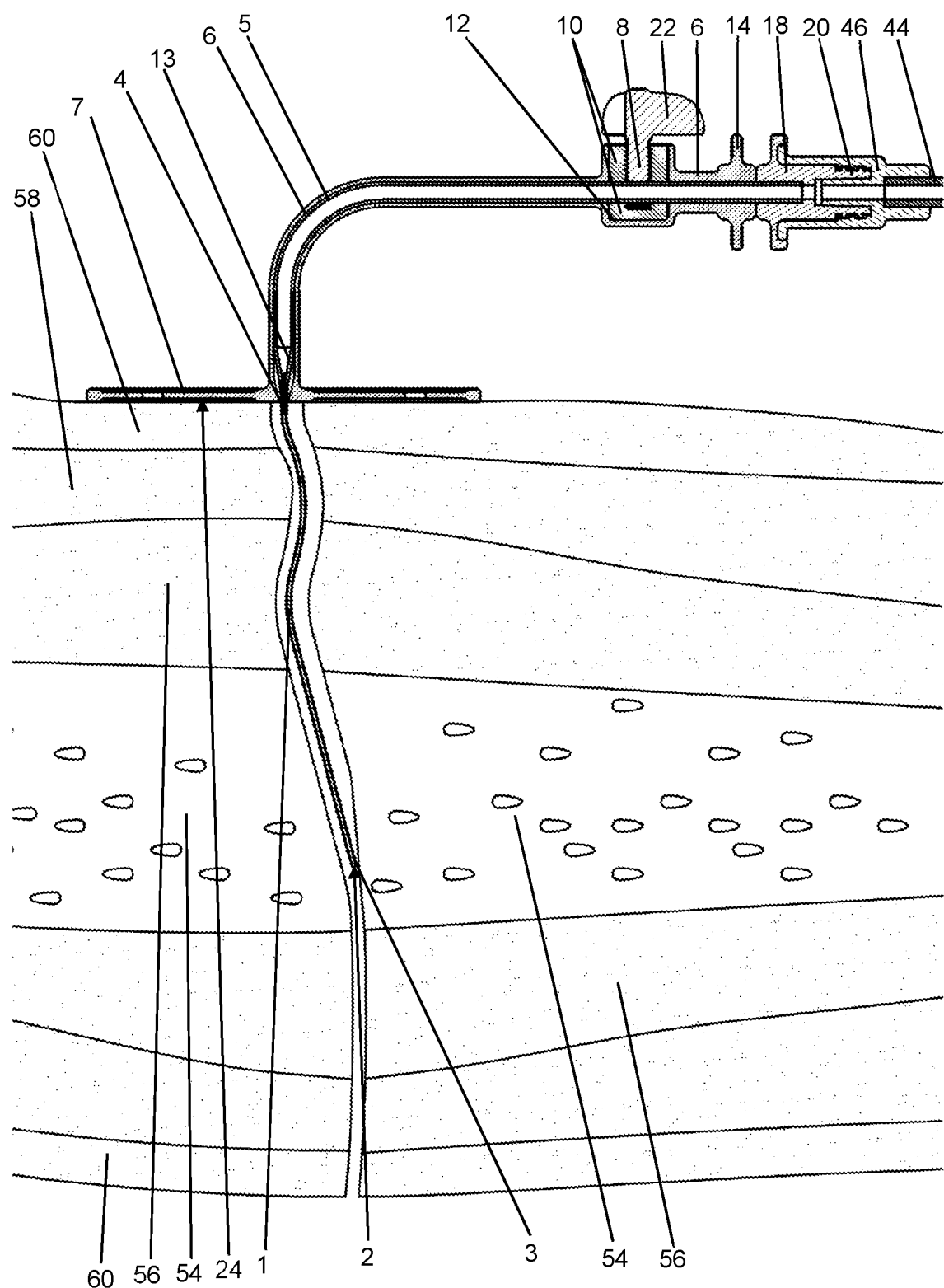
FIG. 10 shows an enlarged detail of FIG. 9.
Figure 14:
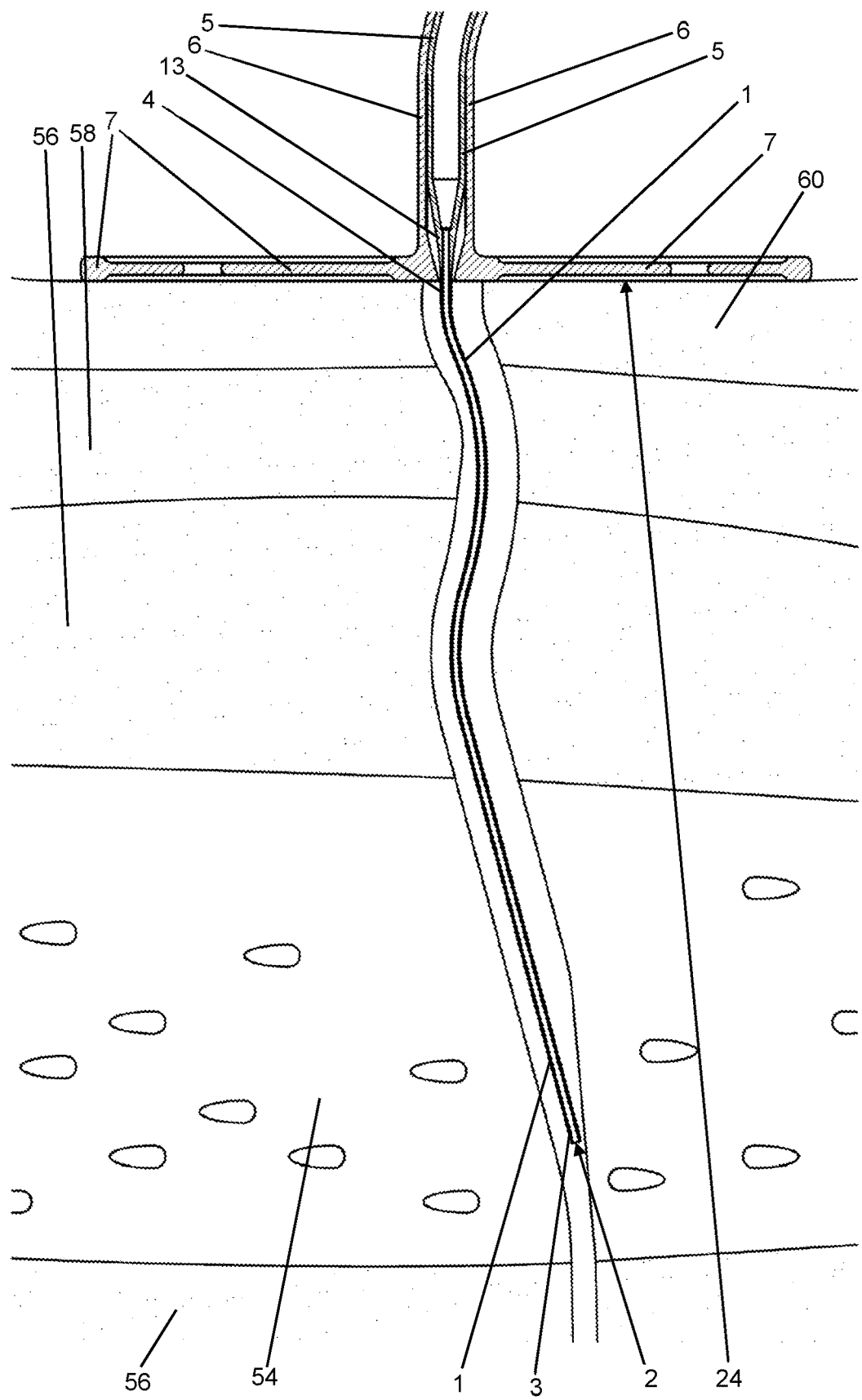
FIG. 14 shows an enlarged detail of FIG. 9.

The capillary 1 may previously be inserted into a gap in an aligned fracture or into a bore. In this case, the capillary 1 may be adapted to the anatomical conditions by plastic deformation or by elastic deformation. The device may in this case be fixed on the surface of the patient by fixing the support 7 to the patient's skin 60 with adhesive strips or plasters (not shown). Alternatively, the support 7 may also be sewn onto the patient's skin 60. The capillary 1 may extend through the skin 60, through the soft tissue 58, and through the bone 56 into the medullary cavity 54 of the patient to be treated. The opening 2 of the capillary 1 may be arranged in the medullary cavity 54. This situation is shown in FIGS. 9, 10 and 14.

In this way, the pharmaceutical fluid may be passed by the capillary 1 through the opening 2 into the medullary cavity 54 and there be used for medical treatment. On termination of treatment, the capillary 1 may be removed from the patient and the wound opening can heal. To prevent microorganisms from invading during treatment, a sponge or a nonwoven fabric (not shown) containing a disinfectant or an antiseptic may be arranged at the distal end of the support 7.

The capillary 1 may consist of a special steel or plastic material. The intermediate piece 5 may consist of special steel or plastic material. The guide 6 preferably consists of plastic material. The plastic material may contain a metal reinforcement for better plastic deformability of the guide 6.

The remaining parts, such as the syringe 26 and the tube 44, may be made of plastic material.

Figure 11:
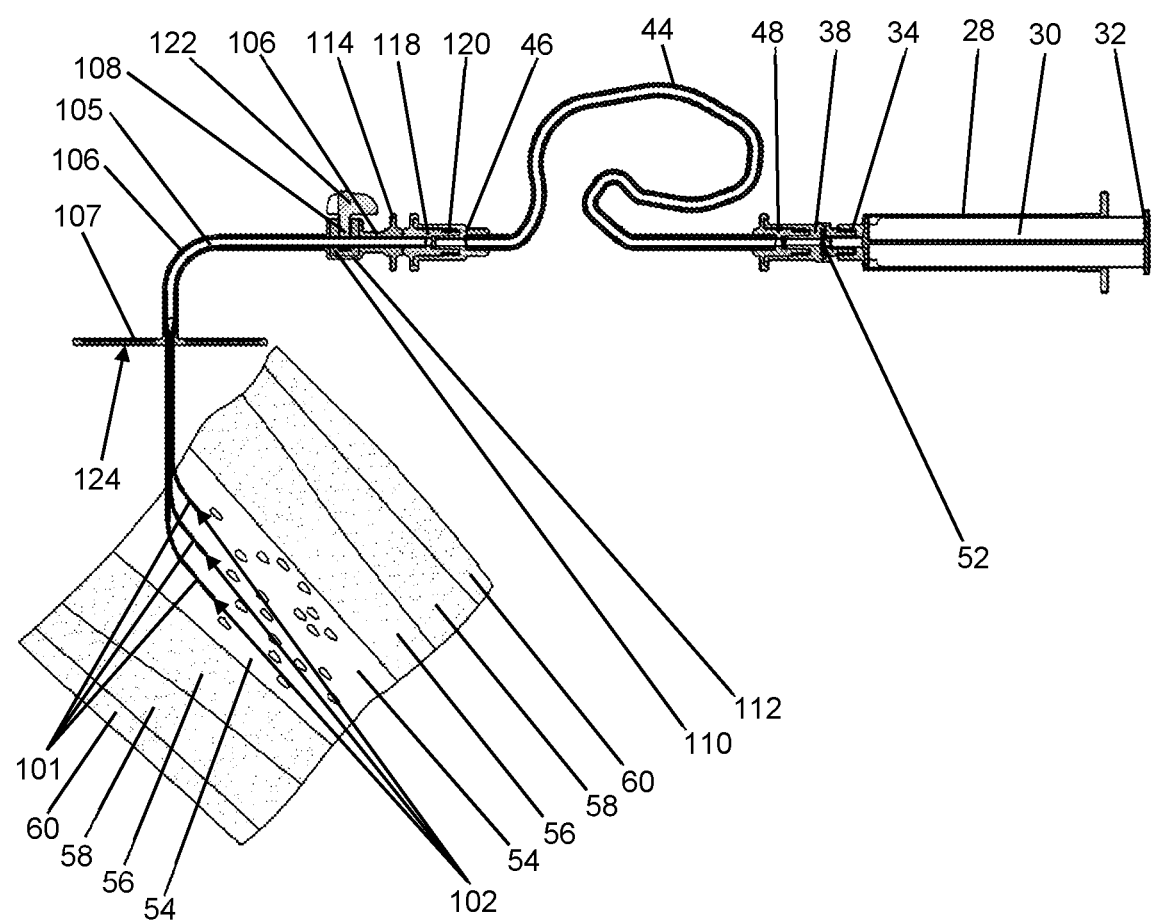
FIG. 11 shows a schematic cross-sectional view of the second device according to the invention during treatment with a syringe connected via a tube and squeezed.
Figure 12:
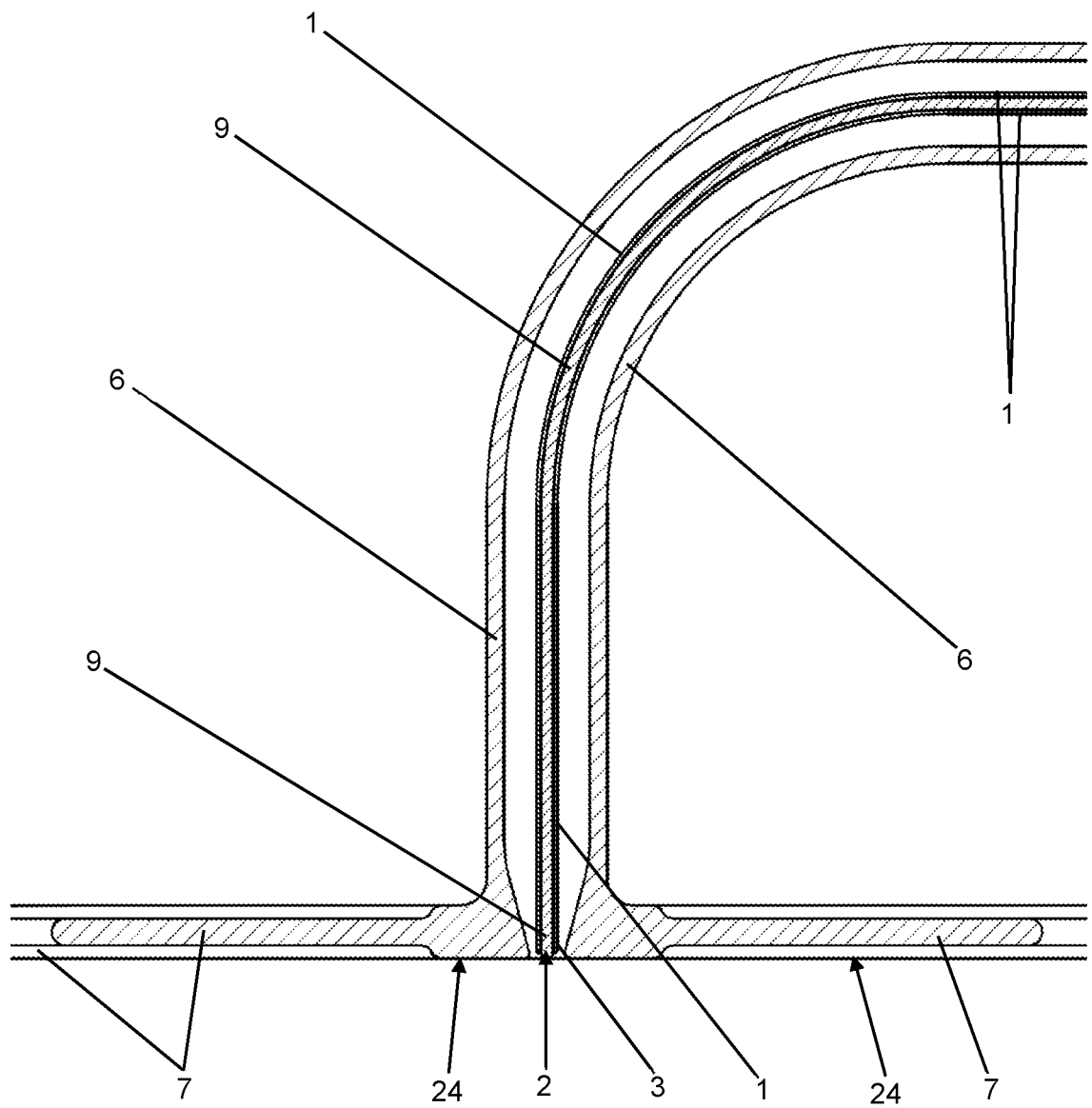
FIG. 12 shows an enlarged detail of FIG. 1.
Figure 13:
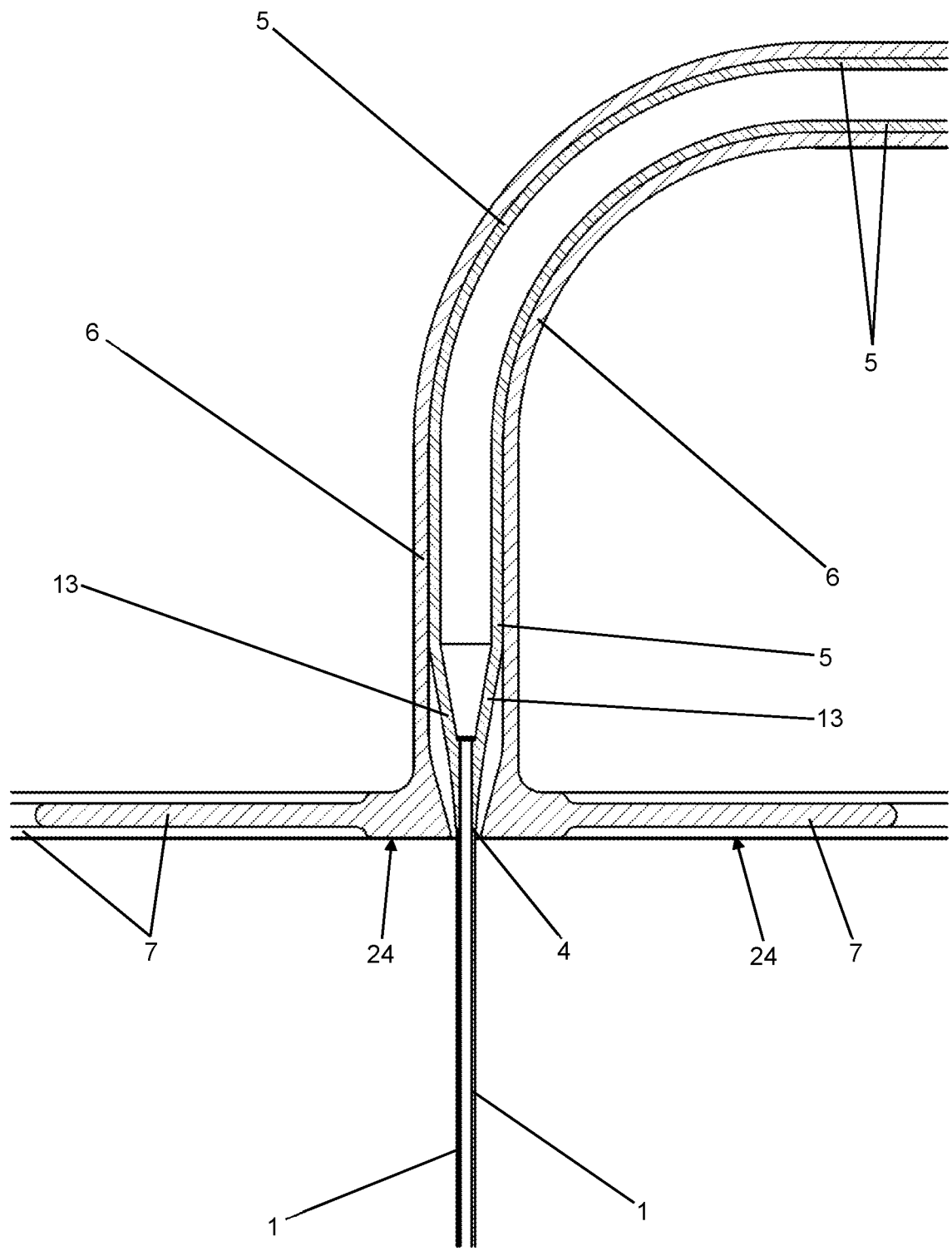
FIG. 13 shows an enlarged detail of FIG. 4.
Figure 15:
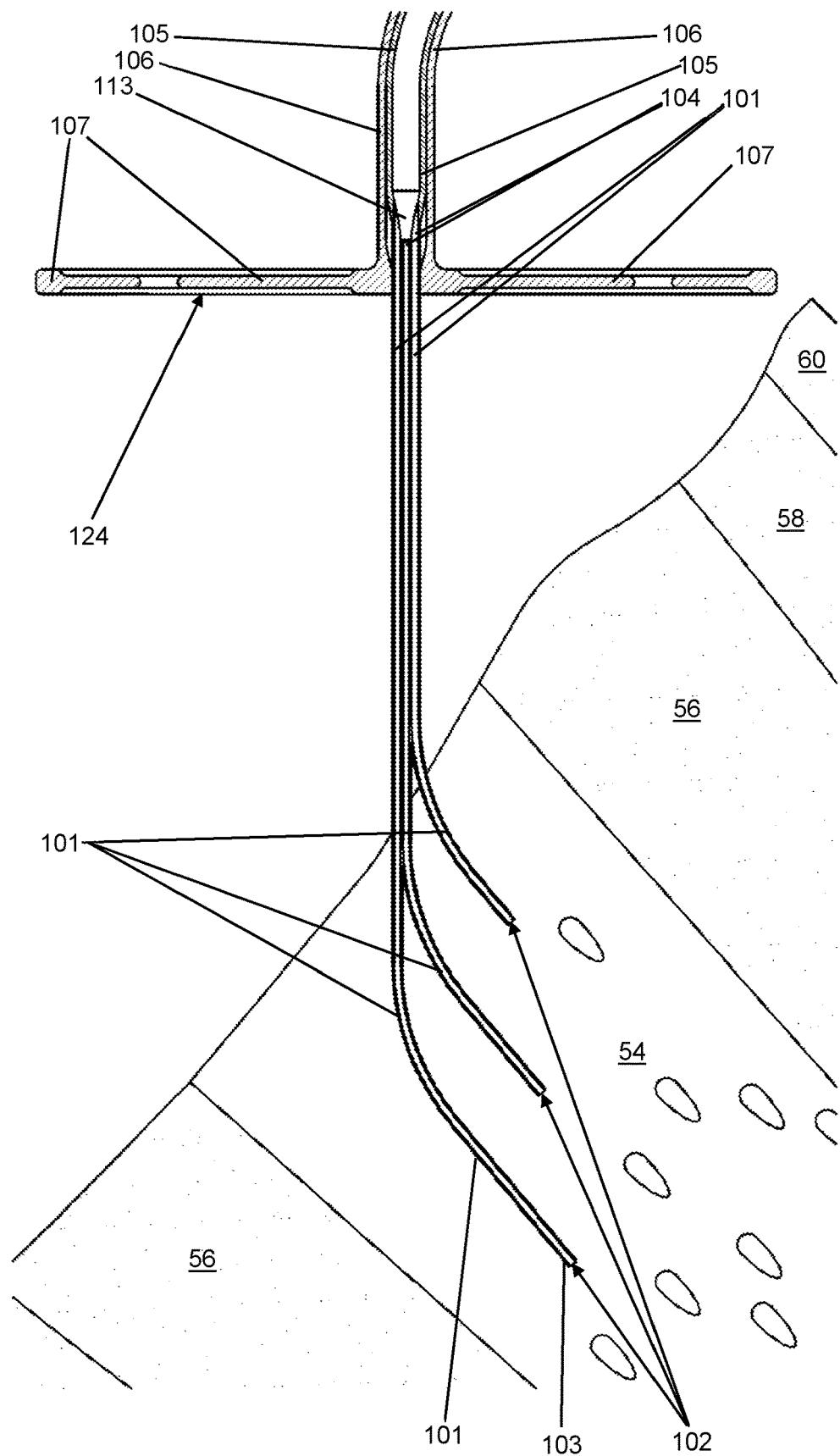
FIG. 15 shows an enlarged detail of FIG. 11.

FIGS. 11 and 15 show schematic cross-sectional views of a second example device according to the invention, which, in contrast to the first example device according to the invention, comprises not just one but three capillaries 101 for administering a medical fluid. Each of the three capillaries 101 has an opening 102 in the distal end 103 of the capillaries 101. However, a plurality of openings (not shown) may also be provided in the walls of the capillaries 101.

The second example device according to the invention is shown inserted into a patient. However, the position in the body of the patient is only shown symbolically. The device would normally not be applied to a severed limb, as might be concluded from FIGS. 11 and 15. The insertion situation corresponds much more to that of FIGS. 9, 10, and 14. The second example device according to the invention is thus preferably used in such a way that the openings 103 of the capillaries 101 are arranged at different sites in the medullary cavity 54 of the bone 56 and/or in the bone 56 and open into the medullary cavity 54 or the bone 56.

With the second example device according to the invention the pharmaceutical fluid can be delivered at different depths or to different sites in the patient's medullary cavity 54 and/or bone 56.

At opposite, proximal ends 104 of the capillaries 101 to the distal ends 103, the capillaries 101 are connected with a hollow intermediate piece 105. Each of the capillaries 101 delimits a cavity in its interior. The cavities of the capillaries 101 may be connected with the cavity in the intermediate piece 105. In this way, the cavities of the capillaries 101 may be connected in a fluid-conducting manner with the cavity of the intermediate piece 105, such that a medical fluid can be forced through the intermediate piece 105 into the capillaries 101 and expelled through the openings 102 of the capillaries 101 at different sites.

The capillaries 101 may preferably in part be combined into bundles. To this end, the capillaries 101 may be connected together as they exit from the intermediate piece 105. The connection may extend as far as the distal ends 103 of the capillaries 101. Preferably, however, the connection extends only as far as roughly half the length of the capillaries 101.

The intermediate piece 105 may be firmly connected with the capillaries 101. The intermediate piece 105 and the capillaries 101 are arranged and guided in a plastically deformable guide 106. To this end, the intermediate piece 105 and the capillaries 101 are arranged movably within the guide 106. At its distal end the guide 106 has a support 107 in the form of a disk. The support 107 may be fastened to a patient, in order to fix the device to the patient. The support 107 has a plurality of holes, which allow gas exchange between the patient's skin 60 and the surroundings. The support 107 is thus placed onto the skin 60 when in use and is not free-floating, as shown merely schematically in FIGS. 11 and 15. The distal bottom and also the proximal top of the support 107 may have recesses. Into these recesses a sponge (not shown) in the form of a circular disk (optionally with holes) may be inserted, which may be impregnated with a disinfecting solution. In this way, the surface of the skin 60 and thus the entrance site of the capillaries 101 into the patient's body may be kept free of microorganisms. The sponge may be part of the device.

A fixing element 108 for fixing the intermediate piece 105 on the guide 106 is arranged in the guide 106. When the intermediate piece 105 is fixed on the guide 106 by the fixing element 108, the intermediate piece 105 can no longer be moved in relation to and in the guide 106 and the capillaries 101 can consequently no longer be displaced axially in relation to the guide 106.

In the initial state (not shown in FIGS. 11 and 15), a withdrawable core (not shown but similar to the first exemplary embodiment) can be arranged inside the capillaries 101 and the intermediate piece 105, which core closes the openings 102 of the capillaries 101. Unlike the core 9 according to the first exemplary embodiment, the core of the second exemplary embodiment may be split up into multiple branches, wherein the branches arranged in the capillaries 101 have a smaller internal diameter than the capillaries 101. The openings 102 are preferably at least 50% closed. The core or the branches of the core may to this end project through the openings 102 out of the capillaries 101, so as to compensate for movement of the core in relation to the openings 102 on bending of the capillaries 101. It may to this end be sufficient for the core to protrude by at most 3 mm out of the openings 102 of the straight capillaries 101, preferably for the core to protrude by at most 1 mm out of the openings 102 of the straight capillaries 101. The core may be withdrawn from the proximal end of the intermediate piece 105 in order to open the openings 102 of the capillaries 101.

The fixing element 108 may have an outer thread and be screwed into a matching seat 110 with an inner thread in the manner of a screw in order to fix the intermediate piece 105 in the seat 110 and thus to the guide 106. To this end, the intermediate piece 105 may be guided through the seat 110. The guide 106 has a receptacle 112 in which the seat 110 is inserted or fastened.

A hollow cone 113 is arranged at the point of transition from the intermediate piece 105 to the capillaries 101. The hollow cone 113 allows the cavities of the capillaries 101 and of the intermediate piece 105 to be connected together and merge with one another. To this end, the interior of the hollow cone 113 may taper conically towards the cavity of the capillary 101. The capillaries 101 may be connected with the intermediate piece 105 via the conical wall of the hollow cone 113.

A limit stop 114 in the form of a protruding disk, which simplifies handling of the device, is arranged at a proximal end of the guide 106.

In the initial state (not shown in FIGS. 11 and 15), the core may be connected at its proximal end with a fastening cap (not shown), which may be screwed onto an adapter 118 with a matching outer thread 120. To this end, an inner thread matching the outer thread 120 of the adapter 118 may be arranged in the fastening cap. The adapter 118 may be fastened to the proximal end of the intermediate piece 105. The fastening cap and the adapter 118 connect the core with the intermediate piece 105 and thus with the capillaries 101. By unscrewing the fastening cap from the adapter 118, the core may be released from the intermediate piece 105 and the capillaries 101. After release of the fastening cap, the core may be withdrawn from the intermediate piece 105 and the capillaries 101, as in the first exemplary embodiment. In this way, the cavities inside the capillaries 101 and the intermediate piece 105 can be opened and the openings 102 are opened. This prevents the openings 102 from being obstructed or clogged by soiling before removal of the core.

The fixing element 108 may be operated, or unscrewed and released, by using a twist handle 122. Once the fixing element 108 has been released using the twist handle 122, the intermediate piece 105 may be moved in relation to the guide 106.

The distal bottom of the support 106 forms a support face 124 for resting on the skin 60 or surface of a patient.

A syringe 26 (right in FIGS. 11 and 15) may be part of the device but also a separate part with which a pharmaceutical fluid may be injected into the device. The syringe 26 comprises a container 28 with a cylindrical interior for the pharmaceutical fluid. A plunger 30 is arranged axially movably in the cylindrical interior of the container 28. The plunger 30 may be pushed into the container 28 by using a plunger flange 32 in order to expel a medical or pharmaceutical fluid from the container 28. A connecting piece 34 with an inner thread is arranged at the front end of the syringe 26, so as to be able to connect the syringe 26 with the adapter 118. A closure 36 for closing the interior of the container 28 at the front end of the container 28 is arranged at the tip of the connecting piece 34.

To connect the connecting piece 34 with the adapter 118 of the intermediate piece 105, a connecting adapter 38 with an outer thread 40 is provided. The outer thread 40 of the connecting adapter 38 may be used to produce a fluid-tight connection with the inner thread of the connecting piece 34 of the syringe 26. In this way, a fluid-tight connection between the interior of the container 28 of the syringe 26 and the cavity of the intermediate piece 105 may be produced by using the connecting adapter 38.

To extend the connection between the syringe 26 and the intermediate piece 105, a tube 44 is used. The tube 44 also has the advantage that it is deformable, such that on connection of the syringe 26 with the intermediate piece 105 via the tube 44, no forces are transferred from the syringe 26 to the intermediate piece 105 provided the tube is loose and not taut. The tube 44 comprises a counter-adapter 46 for connection with the adapter 118 on the intermediate piece 105. Furthermore, the tube 44 has a connector 48 for connection with the connecting adapter 38. In this way, the tube 44 provides a fluid-tight connection between the syringe 26 and the intermediate piece 105.

A filter 52 is arranged inside the connecting adapter 38, to prevent the passage of particles and/or microorganisms into the intermediate piece 105. This filter 52 is preferably a sterile filter. For the same purpose, a sterile filter (not shown) may be arranged in the adapter 118 or in the distal end of the cavity of the intermediate piece 105.

A method according to the invention proceeds basically in the same way for the second exemplary embodiment as for the first exemplary embodiment. On drawing the core out of the intermediate piece 105 and the capillaries 101, in the second exemplary embodiment not just one but all the openings 102 of the capillaries 101 are opened.

The capillaries 101 may be inserted beforehand into a gap in an aligned fracture or into a bore, wherein the distal ends 103 of the capillaries 101 and thus the openings 102 are placed at different sites. In this respect, the capillaries 101 may be adapted by plastic deformation or by elastic deformation to the anatomical conditions and reach the desired different sites. The device may in this case be fixed to the surface of the patient by fixing the support 107 to the patient's skin 60 with adhesive strips or plasters (not shown). Alternatively, the support 107 may be sewn onto the patient's skin 60. The capillaries 101 may extend through the skin 60, through the soft tissue 58, and through the bone 56 into the medullary cavity 54 of the patient to be treated. The openings 102 of the capillaries 101 may in this way be arranged at all the desired sites in the medullary cavity 54 or in the bone 56. This situation is shown in FIGS. 11 and 15.

In this way, the pharmaceutical fluid may be passed by the capillaries 101 through the openings 102 into the medullary cavity 54 and there be used for medical treatment. On termination of treatment, the capillaries 101 may be removed from the patient and the wound opening can heal. To prevent microorganisms from invading during treatment, a sponge or a nonwoven fabric (not shown) containing a disinfectant or an antiseptic may be arranged at the distal end of the support 107.

The capillaries 101 may consist of a special steel or plastic material. The intermediate piece 105 may consist of special steel or plastic material. The guide 106 preferably consists of plastic material. The plastic material may contain a metal reinforcement for better plastic deformability of the guide 106. The remaining parts, such as the syringe 26 and the tube 44, may be made of plastic material.

In all the embodiments, a solution containing at least one antibiotic or one antimycotic or a mixture of different antibiotics and/or antimycotics can preferably be used as the pharmaceutical fluid.

The features of the invention disclosed in the preceding description, as well as in the claims, figures, and exemplary embodiments, may be essential both individually and in any combination for realizing the invention in its various embodiments. Although illustrated and described above with reference to certain specific embodiments and examples, the present disclosure is nevertheless not intended to be limited to the details shown. Rather, various modifications may be made in the details within the scope and range of equivalents of the claims and without departing from the spirit of the disclosure.

The invention claimed is:

1. A device for local administration of a pharmaceutical fluid to a patient, the device comprising:
   at least one capillary having a distal end and a proximal end and having at least one opening in the distal end of the at least one capillary;
   a hollow intermediate piece having a distal end and a proximal end, the distal end of the intermediate piece directly connected with the proximal end of the at least one capillary to allow the passage of the fluid in an axial direction;
   a guide having a distal end and a proximal end and configured to direct both the intermediate piece and the at least one capillary within the guide, the guide having a distal support at the distal end of the guide that is configured to rest on the patient at an entrance site at which the at least one capillary enters the patient, such that parts of the at least one capillary protruding from the guide are inserted into the patient at the entrance site, wherein the hollow intermediate piece and the at least one capillary are both configured to move coaxially within and to pass through the guide, such that the distal end of the capillary is placed inside the patient at the entrance site and directed by the guide; and
   a fixing element connecting the intermediate piece to the guide in various positions relative to the guide by means of a force from the fixing element directly acting on the intermediate piece while preventing displacement of the intermediate piece in relation to the guide.

2. The device according to claim 1, further comprising a deformable tube which is connected or connectable with the intermediate piece so as to allow passage of the fluid.

3. The device according to claim 1, further comprising a hose connected or connectable with the intermediate piece and configured for passage of the fluid from a fluid reservoir, wherein the fluid is forced out of the fluid reservoir under pressure through the intermediate piece and through the at least one capillary.

4. The device according to claim 1, wherein the intermediate piece is arranged axially movably in the guide when a connection provided by the fixing element is released.

5. The device according to claim 1, wherein:
the fixing element is: a retaining device or clamping device arranged on the guide; or a screw having a front end, and the guide has a wall with a bore extending through the wall and including an inner thread and the screw is screwed or is screwable into the bore such that the intermediate piece is clamped in the guide with the front end of the screw.

6. The device according to claim 1, wherein the intermediate piece allows the passage of the fluid when the intermediate piece is connected by the fixing element to the guide.

7. The device according to claim 1, wherein the guide has a cavity and an axially length of the cavity is at least as long as a length of the at least one capillary or is at least as long as a length of a longest capillary of the at least one capillary.

8. The device according to claim 1, further comprising a container for the fluid, wherein the fluid includes at least one antibiotic active ingredient, at least one antimycotic active ingredient, and/or at least one chemotherapeutic agent.

9. The device according to claim 1, wherein the at least one capillary is at least two capillaries each having a different length.

10. The device according to claim 1, wherein the at least one capillary consists of titanium, steel, or plastic.

11. The device according to claim 1, wherein the at least one capillary is deformable.

12. The device according to claim 1, wherein the guide has a distal end configured to receive a porous sponge-like disk including an antiseptic liquid.

13. The device according to claim 1, wherein the intermediate piece is cylindrical or tubular.

14. The device according to claim 13, wherein the intermediate piece has a distal end which is connected to the at least one capillary and the intermediate piece has a taper at the distal end of the intermediate piece.

15. The device according to claim 1, wherein the guide has a distal end, a cavity that tapers at the distal end, and a hole arranged in the distal end of the cavity at the distal end through which the at least one capillary is guided or guidable through the distal end of the guide.

16. The device according to claim 15, wherein the intermediate piece has an external diameter and the hole has a diameter that is smaller than the external diameter of the intermediate piece.

17. The device according to claim 1, wherein the at least one capillary has a cavity, the intermediate piece has a cavity connected with the cavity of the at least one capillary, and the at least one opening has a cross-sectional area and the device further comprises a core arranged in the cavities of the at least one capillary and of the intermediate piece, wherein the core is removable from the cavity of the at least one capillary, closes at least 50% of the cross-sectional area of the at least one opening, and is releasably connected with the intermediate piece in such a way that axial movement of the core in the cavity of the at least one capillary is limited or prevented when connected.

18. The device according to claim 17, further comprising an adapter configured to draw the core out of the cavity of the at least one capillary.

19. The device according to claim 17, further comprising a thread or a bayonet closure by which the core is releasably connected with the intermediate piece.

20. The device according to claim 17, wherein the core projects beyond the at least one opening in the distal end of the at least one capillary to the extent that, upon bending of the at least one capillary, at least 50% of the cross-sectional area of the at least one opening is closed.

21. A method for preparing a device for local administration of a pharmaceutical fluid using the device according to claim 1 prior to medical use, the method comprising the following steps taking place in a chronological sequence:
(A) pushing the at least one capillary out of the guide by inserting the intermediate piece into the guide in an axial direction; and
(B) fixing the intermediate piece in the guide with the fixing element.

22. The method according to claim 21, further comprising the step (C) after step (A) or after step (B) of shaping the at least one capillary by plastic deformation of the at least one capillary.

* * * * *